(12) United States Patent
Bartsch et al.

(10) Patent No.: US 6,581,915 B2
(45) Date of Patent: Jun. 24, 2003

(54) DISPENSING DEVICE FOR DISPENSING SCENTS

(75) Inventors: Eric Richard Bartsch, Cincinnati, OH (US); Stephan Gary Bush, Sharonville, OH (US); Brice Daniel Westring, Loveland, OH (US); Grover David Owens, Fairfield, OH (US); Frank Andrej Kvietok, Cincinnati, OH (US); Michael Sean Farrell, Maineville, OH (US); Christophe Laudemiel-Pellet, New York, NY (US); Pedro Antonio Rodriguez, Sanibel, FL (US); Toan Trinh, Maineville, OH (US); Kevin George Goodall, Cincinnati, OH (US); Carl-Eric Kaiser, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/730,226

(22) Filed: Dec. 5, 2000

(65) Prior Publication Data

US 2002/0066967 A1 Jun. 6, 2002

Related U.S. Application Data

(63) Continuation of application No. PCT/US00/20499, filed on Jul. 22, 2000.
(60) Provisional application No. 60/251,067, filed on Dec. 4, 2000.

(51) Int. Cl.[7] .................................................. B01F 3/04
(52) U.S. Cl. .......................... 261/26; 261/30; 261/104; 261/142; 261/DIG. 88; 261/DIG. 89; 422/123; 422/124
(58) Field of Search ............................ 261/26, 30, 104, 261/142, DIG. 65, DIG. 88, DIG. 89; 422/123, 124; 239/57, 58, 59

(56) References Cited

U.S. PATENT DOCUMENTS

| 3,410,488 A | 11/1968 | Sugimura |
| 4,549,250 A | 10/1985 | Spector |

(List continued on next page.)

FOREIGN PATENT DOCUMENTS

| CA | 2222838 | 1/1997 |
| EP | 0 295 129 A1 | 12/1988 |

(List continued on next page.)

OTHER PUBLICATIONS

Aromajet Press Release, "Aromajet.com Demonstrates Proof–of–Concept Aroma Generation System for Game Environments", on Aromajet.com web site Jan. 19, 2001.

DigiScents Products, "Our Product 'Sweet'", on DigiScents web site Jan. 19, 2001.

Norelco Consumer Products Company, "Aromatherapy System AT100" instructions, copyright 1996.

UltraScent Products, "The Ultimate Aromatherapy Diffuser—UltraScent the Only Multi–scent Aromatherapy Diffuser", on Bunny Moony Enterprise's web site Aug. 5, 2000.

*Primary Examiner*—Robert A. Hopkins
(74) *Attorney, Agent, or Firm*—Jeffrey V. Bamber

(57) ABSTRACT

A dispensing device for dispensing scents into the environment is disclosed. In one embodiment, the dispensing device is used in conjunction with an article of manufacture which contains one or more scents or aromatic materials. In such an embodiment, the dispensing device can include a housing and a removable, reusable/replayable, closed, multiple scent-containing article of manufacture which is removably inserted into or onto said housing.

69 Claims, 8 Drawing Sheets

U.S. PATENT DOCUMENTS

| | | | |
|---|---|---|---|
| 4,588,874 A | * | 5/1986 | Napierski .................... 239/136 |
| 4,603,030 A | | 7/1986 | McCarthy |
| 4,629,604 A | | 12/1986 | Spector |
| 4,695,434 A | | 9/1987 | Spector |
| 4,714,984 A | | 12/1987 | Spector |
| 4,743,406 A | | 5/1988 | Steiner et al. |
| 5,023,020 A | | 6/1991 | Machida et al. |
| 5,071,621 A | | 12/1991 | Tokuhiro et al. |
| 5,163,616 A | | 11/1992 | Bernarducci et al. |
| 5,167,877 A | | 12/1992 | Pai |
| 5,220,636 A | | 6/1993 | Chang |
| 5,234,162 A | | 8/1993 | Sullivan |
| 5,565,148 A | | 10/1996 | Pendergrass, Jr. |
| 5,662,835 A | | 9/1997 | Collingwood |
| 5,805,768 A | | 9/1998 | Schwartz et al. |
| 5,887,118 A | | 3/1999 | Huffman et al. |
| 5,972,290 A | | 10/1999 | De Sousa |
| 6,024,783 A | | 2/2000 | Budman |
| 6,136,277 A | | 10/2000 | Nardini |
| 6,152,829 A | | 11/2000 | Jaidka |

FOREIGN PATENT DOCUMENTS

| | | |
|---|---|---|
| EP | 1 205 192 A1 | 5/2002 |
| EP | 1 205 193 A1 | 5/2002 |
| EP | 1 205 194 A1 | 5/2002 |
| EP | 1 205 195 A1 | 5/2002 |
| WO | WO97/02076 | 1/1997 |
| WO | WO 99/08174 | 2/1999 |
| WO | WO00/12143 | 3/2000 |
| WO | WO00/15268 | 3/2000 |
| WO | WO00/15269 | 3/2000 |
| WO | WO01/07093 A1 | 2/2001 |
| WO | WO 01/19417 A1 | 3/2001 |
| WO | WO 02/38192 A1 | 5/2002 |
| WO | WO 02/38193 A1 | 5/2002 |
| WO | WO 02/38194 A1 | 5/2002 |
| WO | WO 02/38195 A1 | 5/2002 |

* cited by examiner

DISPENSING DEVICE FOR DISPENSING SCENTS

This application is a continuation-in-part of PCT application Ser. No. US00/20499, filed Jul. 22, 2000, the international application published in English, and claims benefit to provisional U.S. patent application Ser. No. 60/251,067, filed Dec. 4, 2000. The present invention relates to a dispensing device for dispensing scents into the enviroment.

FIELD OF THE INVENTION

The present invention relates to a dispensing device for dispensing scents into the environment.

BACKGROUND OF THE INVENTION

Devices are currently available for dispensing a single scent into a room and in automobiles. Examples of such devices include GLADE PLUG INS® plug in room fresheners manufactured by S. C. Johnson.

Devices capable of dispensing a single scent are also described in the patent literature. For example, U.S. Pat. Nos. 4,549,250 and 4,714,984, issued to Spector describe a night light assembly which plugs into an electrical wall outlet. The assembly, when switched on, produces low-level illumination and at the same time exudes an aromatic vapor. The night light assemblies described in these patents also include a picture on the cover thereof of an object, such as a flower, possessing a characteristic odor, to which the fragrance of the aromatic vapor is thematically related.

Devices that are only capable of dispensing a single scent suffer from the drawback that, after a relatively brief period of time, people become used to the scent and do not tend to notice it as much as when the device is first activated. In other words, "fragrance fatigue" can occur whereby a person's olfactory organ becomes "saturated" with a particular smell or fragrance and the individual becomes insensitive to the presence of the particular fragrance.

Therefore, some efforts have been directed toward developing devices capable of emitting a single scent that address the problem of fragrance fatigue. For example, U.S. Pat. No. 4,695,434 issued to Spector discloses an aroma-generating unit that is adapted to periodically discharge into the atmosphere bursts of aromatic vapor. The non-aromatic intervals between the bursts are said to have a duration sufficient to avoid densensitizing the olfactory response of those exposed to the unit. The unit makes use of replaceable cartridges having a mat impregnated with an aroma-producing liquid. The unit has an electrical heater that heats air in a confined chamber, and the heat generated causes the air to expand to create a pressure differential forcing the hot air through the mat. The cartridge is provided with a seal in the form of a detachable metal or plastic clip that fits over the holes in the sheets covering the impregnated mats so that the cartridge, when stored, is sealed to prevent the loss of liquid. The user of the unit may be provided with a stack of sealed cartridges, each of which may have mats impregnated with a different aroma-producing liquid. The user, therefore, may select a fragrance appropriate to the room or to a given occasion.

Other efforts have been made to develop devices that are capable of emitting multiple scents. A number of patents have been directed to devices that are capable of emitting multiple scents.

U.S. Pat. No. 4,629,604 issued to Spector, while not addressing the issue of fragrance fatigue, is directed to a multi-aroma cartridge player. The multi-aroma cartridge player uses a cartridge that comprises a planar array that forms a multi-section framework. Each section of the framework comprises a pad of absorbent material which is impregnated by a liquid fragrance that are said to differ from those of the other sections of the cartridge. The absorbent materials each have a central zone that is exposed. The aroma cartridge player comprises an individual electric heater for each frame assembly containing an individual scent. The selection of the aromas to be played may be effected manually, electronically, or it may be synchronized to follow the scenes of a video tape or movie film presentation.

U.S. Pat. No. 5,805,768 entitled "Aroma Therapy Diffuser" issued to Schwartz, et al. and assigned to Bunny Moon Enterprises of Van Nuys, Calif. describes an aroma therapy diffuser which offers the user the ability to pre-select a variety of different an aromas to be introduced into an environment at pre-selected time intervals. The device includes a tray with a plurality of receptacles for receiving aromatic materials arranged along the periphery of the tray and a means for heating a selected receptacle and the material contained therein. The apparatus also includes a timer and a means for rotating the receptacles about the heating means to expose a selected receptacle to the environment for a pre-selected time period. The apparatus further includes a lid with an opening which exposes selected aromatic material so the aroma released by the heated aromatic material emanates into the environment. The remaining aromatic materials which are not exposed to the heating means are sealed to prevent evaporation.

The device described in the Schwartz, et al. patent, however, apparently contemplates that upon using the scents in the tray, the receptacles for the scents will be cleaned out, and new scents will be placed therein. This has the drawback that it is not convenient for a user to clean and replace the scents. Also, the device currently in the marketplace uses a two hour interval which allows the user's nose to become accustomed to the scent, allowing the experience to fade into the background. The device described in the Schwartz, et al. patent also provides a means for sealing the plurality of receptacles except for one receptacle so that the aromatic materials in the tray do not evaporate. However, the means for sealing the receptacle comprises a lid that remains in the device when the tray of scents is removed. This means is subject to the disadvantage that the aromatic material in the receptacles will not be sealed and will evaporate when the tray is removed. Thus, the tray cannot be removed and later used without the aromatic materials evaporating.

Another device capable of emitting multiple scents is described in PCT Publication WO 97/02076 and Canadian Patent Application 2,222,838, both entitled "Device and Process for Delivering Substances for Dispersal in the Air". The device comprises a flat disc through which pass a number of separate radially oriented channels that receive substances intended for dispersal. Each of the channels has one inlet aperture and one outlet aperture. The channels allow the passage of a gas stream introduced via the inlet aperture. The odoriferous substances, which may be partly the same or all different, are introduced into the channels, or the odoriferous substances are introduced in gas tight reservoirs which are placed in the channels wherein each reservoir releases the individual odoriferous substance only when it is to be dispersed.

The device and cartridge described in PCT Publication WO 97/02076, however, suffers from the drawback that each odoriferous substances are also subject to evaporation after initial use because after rupture of the apertures and/or reservoir by the first use of one specific channel will allow unrestricted and uncontrolled, respectively, passage of an air stream and uncontrolled flow of the odoriferous substance from the channel.

Another device capable of emitting multiple scents is described in PCT Publication WO 00/121143 entitled "Odor Dispensing Device and Odor Dispensing Cartridge". The odor dispensing device described in PCT Publication WO 00/121143 comprises a housing and a disc shaped dispensing cartridge adapted to move around its rotation axis and having a plurality of discrete radically arranged compartments. The cartridge has a body with compartments separated by walls. The compartments are tightly closed and opened by individual covers. The odor dispensing device is said to utilize any mechanical means, such as a fan to emit the odors. While the description of the odor dispensing device and cartridge in PCT Publication WO 00/121143 attempts to distinguish the technology therein as being more simple to manufacture than the technology in a prior publication, it is still a complicated arrangement. While PCT Publication WO 00/121143 describes the composition of the scent materials, it describes nothing about the type of scents that can be placed therein.

There are drawbacks associated with the devices described in all of the foregoing patent publications. None of the devices are believed to describe a system and method for dispensing multiple scents into the environment which enables the scent-containing component of the system to be taken out of the device, replaced with another scent-containing component, and later re-used or replayed without either subjecting the scents to evaporation when the scent containing component is removed, or providing a complicated arrangement for closing the scents from the environment. None of the devices are believed to describe a system and method for dispensing multiple scents into the environment in which the multiple scents on a given scent containing article are related to each other so as to share a common scent theme or sensory experience. Improvements in the controls of multiple scent dispensers are also possible.

Thus, a need exists for a system for dispensing multiple scents that enables the scent-containing component of the system to be taken out of the device, replaced with another scent-containing component, and later re-used or replayed without either subjecting the scents to evaporation when the scent containing component is removed, or providing a complicated arrangement for closing the scents from the environment. A need also exists for a dispensing device for dispensing multiple scents sequentially into the environment that permits the scents in the device to be more conveniently replenished.

In addition, a need exists for a system for dispensing multiple scents that provides scents which are compatible with the system, and with each other, as opposed to a device which requires a user to purchase different perfume oils, which may or may not be compatible, and pour or otherwise place these perfume oils into a device.

A need also exists for a system for dispensing multiple scents which permits the user to control, and if desired vary, the time frequency or period for which each scent is emitted.

The present invention will become more readily apparent when considered in reference to the following description and when taken in conjunction with the accompanying drawings.

SUMMARY OF THE INVENTION

This invention relates to dispensing scents into the environment. In several embodiments, this invention relates to systems or methods, and/or devices or articles for dispensing multiple scents into the environment. Several non-limiting embodiments are described herein, as are several components of the system, each of which may constitute an invention in its own right or together with other components.

In one embodiment, the system for dispensing scents into the environment includes an apparatus, such as a dispensing device and an article of manufacture containing one or more scents or aromatic materials for use in conjunction with the dispensing device. In preferred versions of this embodiment, the scent-containing article of manufacture is able to be removed from the device, replaced with another scent-containing article of manufacture, and later re-used or replayed without either subjecting the scents to evaporation when the scent-containing article of manufacture is removed, and without providing a complicated arrangement for closing the scents from the environment.

The dispensing device can be any device that is capable of dispensing scents or aromatic materials that are either contained in or on the dispensing device, or contained in or on an article of manufacture that is intended to be used in conjunction with the dispensing device. The dispensing device may contain a component for activating the scents or aromatic materials from their "resting" state to an activated state. Such a component may include, but is not limited to a component that volatilizes or heats the scents or aromatic materials. The dispensing device may also contain a component, such as a fan, for diffusing or transporting the aromatic materials into the environment or atmosphere.

The dispensing device may have a number of additional features, which include, but are not limited to one or more of the following features, and other features. If a scent-containing article of manufacture is used in conjunction with the dispensing device, the dispensing device may have a mechanism for locking and unlocking the scent-containing article of manufacture. The dispensing device may have an emission program which is designed to minimize "fragrance fatigue" or "habituation". Improved controls can also be provided.

The scent-containing article of manufacture may be in any suitable form. The article of manufacture may have a configuration which is: disc-shaped, oval, parallelpiped-shaped, rectangular, cube-shaped, cuboid-shaped, cylindrical-shaped, pyramid-shaped, spherical-shaped, irregularly-shaped, or which has some other configuration. In one embodiment, the article of manufacture is a cartridge.

In one aspect of the invention, the article of manufacture is removable from the dispensing device and reusable after it has been removed from the dispensing device. In order to make the article of manufacture is reusable, the scents contained therein or thereon may be sealed when the article is removed from the dispensing device to minimize evaporation of the scents between uses of the scent-containing article. In one non-limiting embodiment, the article of manufacture may have a closed structure with a single opening therein for the emission of scents. In another aspect, the article may comprise multiple scent-containing receptacles. These multiple scent-containing receptacles may be closed with a single sealing mechanism that seals the receptacles when the article is not in use. In another aspect of the invention, the article comprises a locking mechanism which locks the article when it is removed from the device. In one aspect of such an embodiment, the locking mechanism may prevent access to the scents or aromatic materials when the article is outside the device. In this last aspect, the article may be completely free of openable elements such as doors and the like for accessing the aromatic materials to provide a tamper-proof article.

In another aspect of the invention, the article of manufacture may contain multiple scents that are related to each other. The scents can be related to each other in a manner which is not dependent on some other media, and/or are not designed to be used simultaneously with other media for the relationship between the scents. Any number of the scents can be related to each other in such a manner. For example, at least half of the scents in the article of manufacture can be related to each other, or all of the scents in the article of manufacture can be related to each other. In one variation of this aspect of the invention, the scents are related to each other and selected from a group of types of scents. In another variation of this aspect of the invention, certain of the scents, or all the scents, can be related to each other in that they share a common theme.

In any of the embodiments described herein, the article of manufacture may be modified so that it is a stand-alone unit which is capable of dispensing scents without a dispensing device.

The present invention may also include novel methods and kits. Such methods include, but are not limited to methods of providing multiple scent emitting articles each of which has scents therein or thereon that are related, as well as methods of providing scent-containing articles to consumers and/or institutions which provide the ability to "customize" the scents for the user.

Preferably, the components of the system are in a package in association with a set of instructions that direct the consumer how to use, e.g., the diffuser and/or the cartridges correctly, to obtain the desirable olfactory, psychological and/or physiological effects. It is preferable that the apparatus is operated in accordance with the instructions for use, to ensure that the consumer knows what benefits can be achieved, and how best to obtain these benefits. As used herein, the phrase "in association with" means that the instructions are either printed directly on the components themselves and/or on their packages, or presented in a different manner including, but not limited to, a videotape, a brochure, print advertisement, electronic advertisement, and/or verbal communication, so as to communicate the set of instructions to a consumer of the article of manufacture. It is important that the instructions be simple and clear. The use of pictures and/or icons within the instructions may be desirable.

In any of the embodiments described herein, the article of manufacture may be configured partially, or completely for recycling.

Numerous other embodiments are also possible, including, but not limited to those described in the following detailed description.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

I. Introduction (The Scent Dispensing System and Apparatus)

This invention relates to dispensing scents into the environment. In several embodiments, this invention relates to systems or methods, and/or devices or articles for dispensing multiple scents into the environment. Several non-limiting embodiments are described herein, as are several components of the system, each of which may constitute an invention in its own right or together with other components. The scents or aromas can be supplied to various facilities, which include but are not limited to rooms, houses, hospitals, offices, theaters, buildings, and the like, or into various vehicles such as trains, subways, automobiles, airplanes and the like.

The terms "aroma" and "scents", as used herein, include, but are not limited to pleasant or savory smells, and, thus, also encompass scents that function as insecticides, air fresheners, deodorants, aromacology, aromatherapy, insecticides, or any other odor that acts to condition, modify, or otherwise charge the atmosphere or to modify the environment.

In one embodiment, the system for dispensing scents into the environment comprises one or more components containing one or more scents or aromatic materials. In such an embodiment, the system preferably comprises a dispensing device, such as diffuser and one or more scent-containing articles of manufacture, which may be provided in the form of fragrance "cartridges". Each cartridge can provide a combination of different scents, preferably, each of the cartridges provides a collection of scents that conveys, e.g., a theme, and experience, a physiological effect, and/or a therapeutic effect.

It is known that the perceived intensity of a released fragrance decreases with time from the instant of fragrance emission and therefore repeated release of fragrance can be necessary to maintain a desired fragrance intensity. It is also known that "fragrance fatigue" can occur whereby a person's olfactory organ becomes "saturated" with a particular smell or fragrance and thus the individual becomes insensitive to the presence of the particular fragrance. The system and apparatus are especially useful for overcoming this fragrance fatigue that occurs with prior devices that are only capable of emitting a single scent, as well as addressing drawbacks with prior devices capable of emitted multiple scents. It should be understood, however, that the present invention is not limited to devices that are capable of emitting multiple scents, since various aspects of the invention are believed to be novel even when used on devices capable of emitting a single scent.

Figure 1:
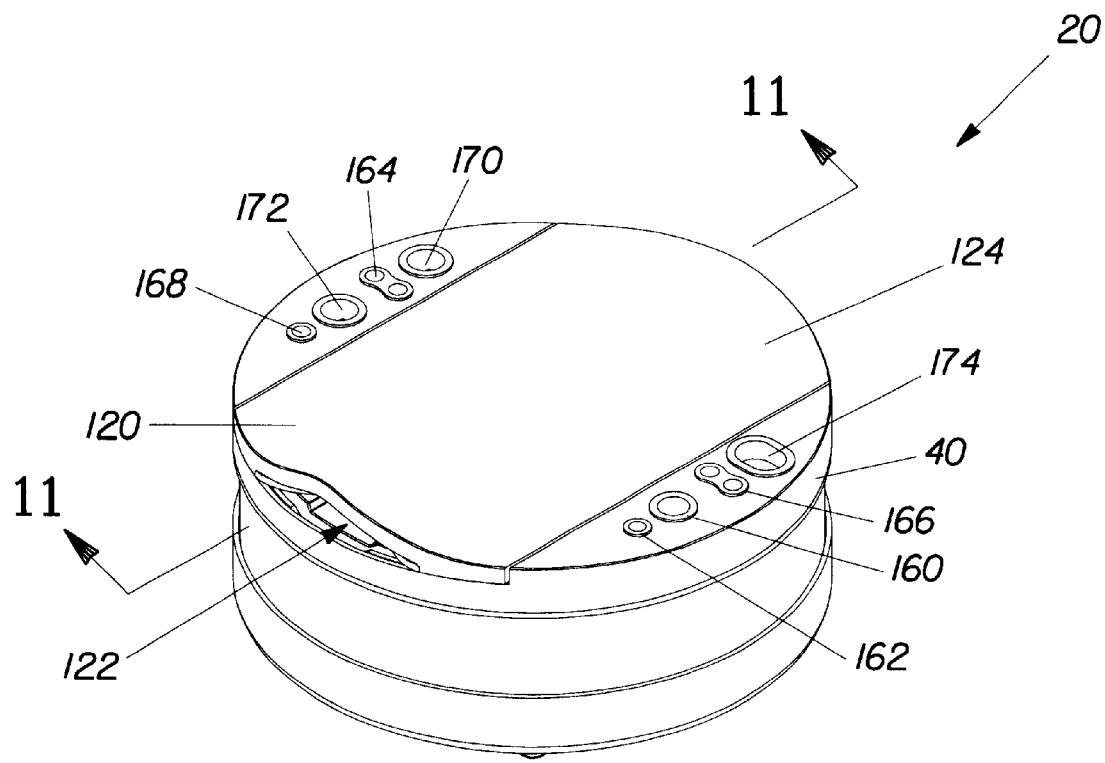
FIG. 1 is a perspective view of one embodiment of the device with the cartridge inserted and the cartridge door in a closed position.
Figure 2:
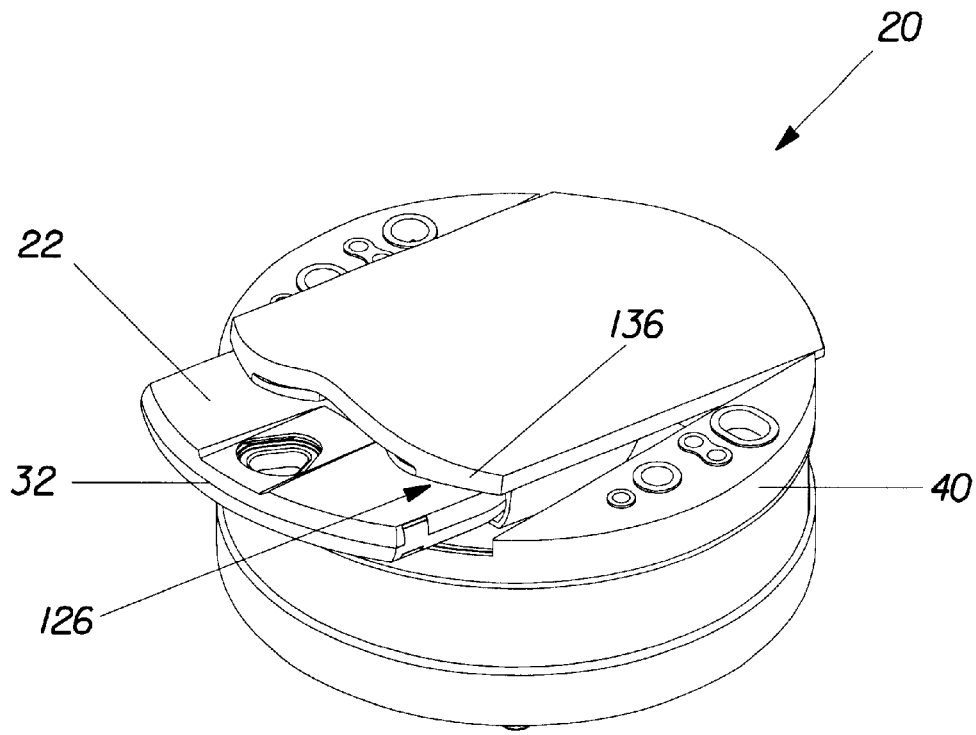
FIG. 2 is a perspective view of the device with the cartridge door in an open position and a cartridge partially removed.
Figure 3:
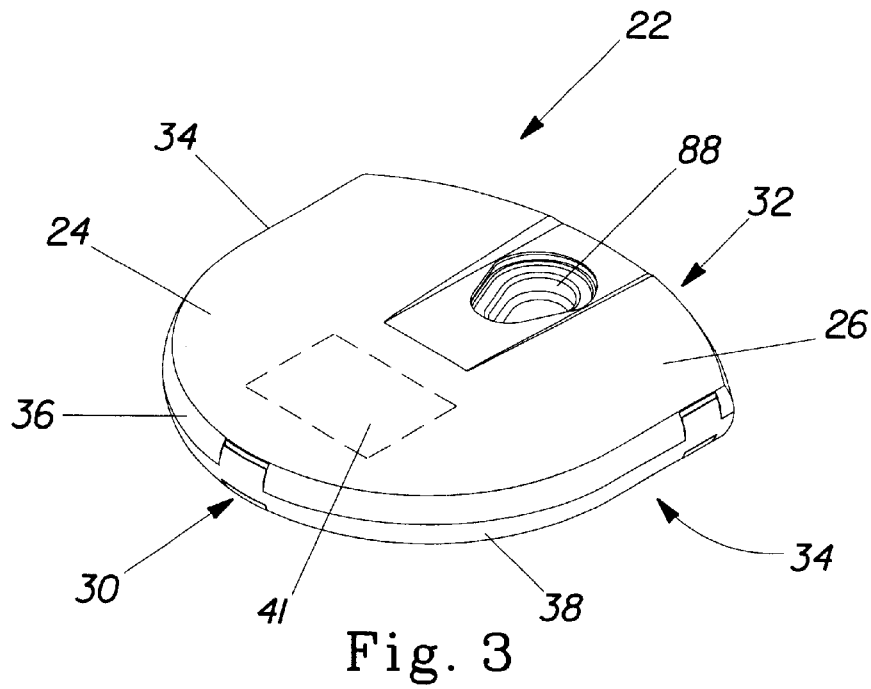
FIG. 3 is a perspective view of one embodiment of a cartridge.
Figure 4:
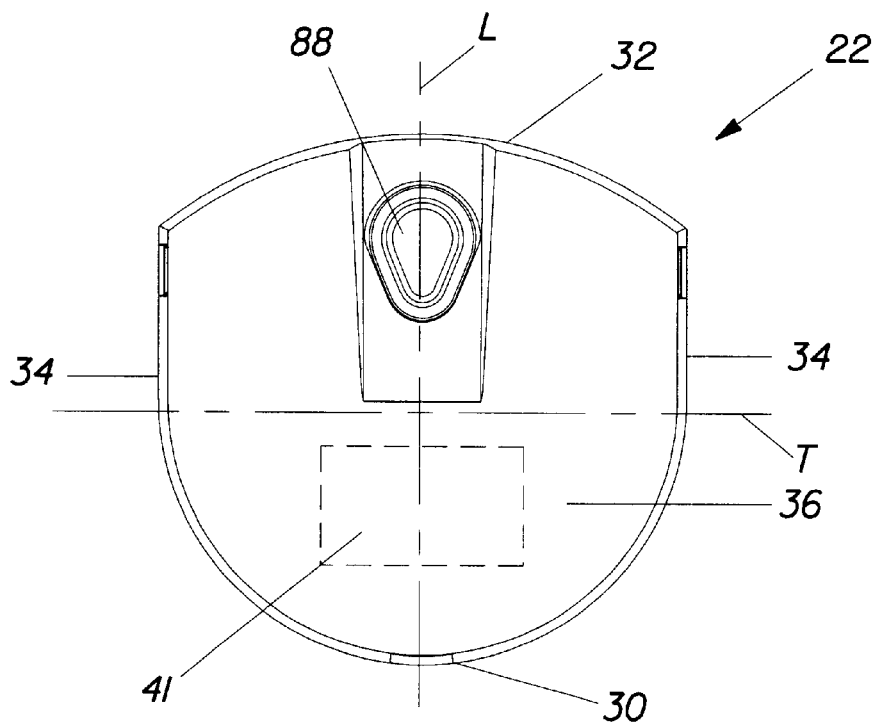
FIG. 4 is a top plan view of the cartridge shown in FIG. 3.
Figure 5:
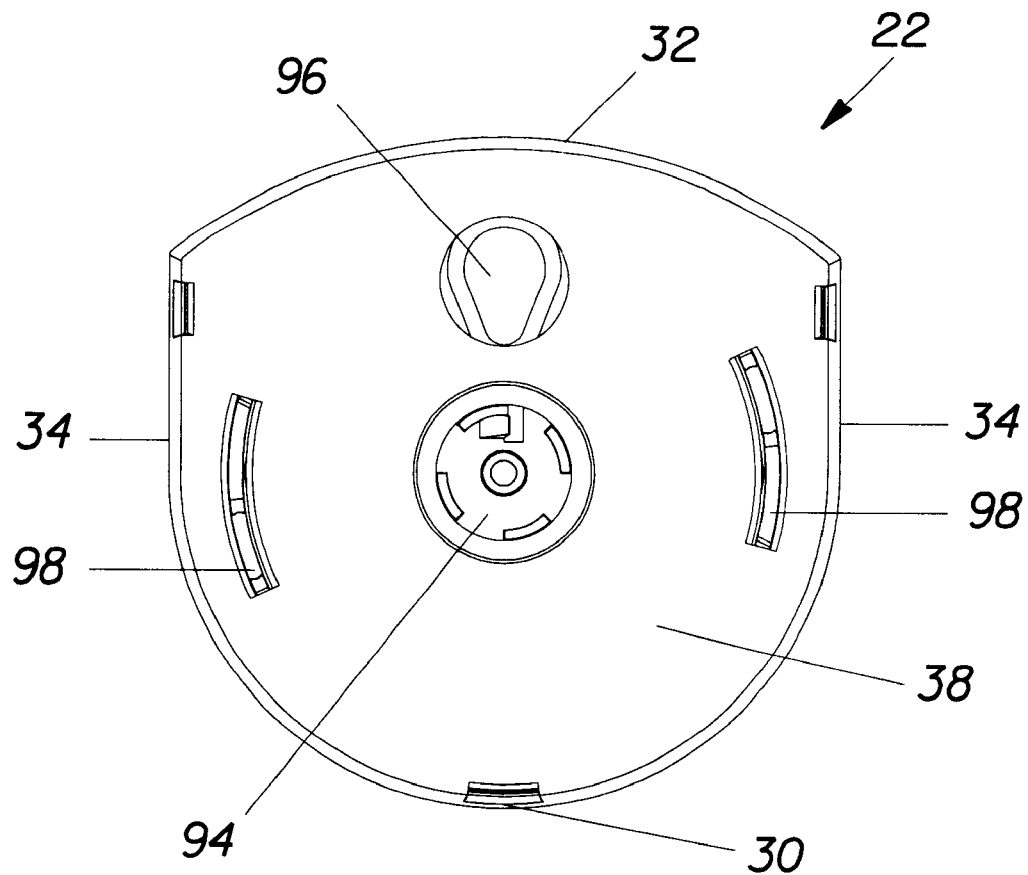
FIG. 5 is a bottom plan view of the cartridge shown in FIG. 3.
Figure 6:
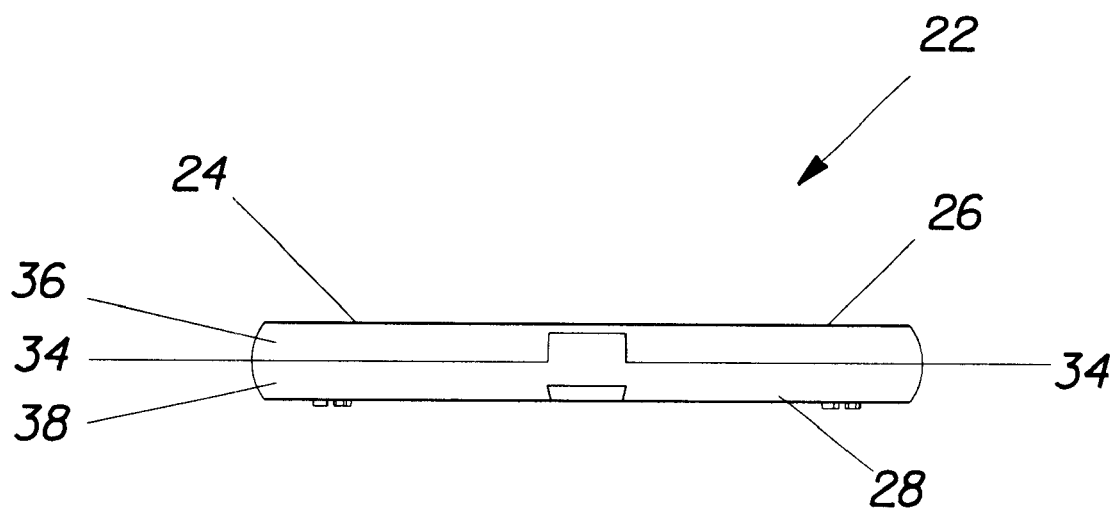
FIG. 6 is a front end view of the cartridge shown in FIG. 3.

FIGS. 1 and 2 show one non-limiting embodiment of the system of the present invention for dispensing multiple scents into the environment. The system comprises an apparatus (or "diffuser", "dispensing device", or simply "device") 20 and a replaceable multiple scent-containing article of manufacture, such as cartridge 22. The drawings show one non-limiting example of the device and the multiple scent-containing article of manufacture. The control buttons for the device are described in greater detail below. The system of the present invention (that is, the device and cartridge) can be provided in many other suitable configurations.

II. The Scent-Containing Article of Manufacture

FIGS. 3–6 show on e non-limiting embodiment of the scent-containing article of manufacture in the form of cartridge 22 as it appears when it is removed from the device 20. The cartridge 22 can contain a single scent or multiple scents, which may be provided in the form of scent elements. The cartridge 22 has a longitudinal centerline L, and a transverse centerline T.

The cartridge 22 comprises a housing portion (or shell) 24, which has a top surface 26, a bottom surface 28, a front end 30, a rear end 32, and sides 34. The cartridge 22 can be of any suitable configuration. In other embodiments, the scent elements may be contained in or on an article that does not resemble the cartridge shown in the drawings. The term "cartridge" as used herein, is not limited to articles that are in the form of cases or cassettes. Such an article could be provided in any suitable configuration. For example, the scent elements could be provided in or on an article that resembles a disk, such as a compact disk (CD), rather than the device shown in the drawings. Examples of other suitable configurations for the scent-containing article of manufacture are set forth above in the Summary of the Invention section. In addition, it should be understood that whenever the term "cartridge" is used herein, this is done merely for the purpose of describing the structure shown in the drawings, and anything that is described relative to the cartridge will also be applicable to other types of articles of manufacture.

In the embodiment shown in the drawings, the cartridge 22 has a front end 30 with a configuration that resembles a circle. The sides 34 of the cartridge, however, are more rectilinear and substantially parallel to each other. The rear end 32 of the cartridge 22 shown in the drawings is convexly curved, but with a curvature that is less than that of the front end 30 of the cartridge 22. The shell 24 of the cartridge 22 comprises an upper portion (or upper half) 36, and a lower portion (or lower has 38. The curvature of the rear end 32 of the cartridge 22 in this embodiment preferably matches the curvature of the outside walls 40 of the dispensing device 20.

The scent-containing article of manufacture, such as cartridge 22, is preferably removable from the device, and closed and sealed (that is, the scents are sealed) so that the scents are protected from evaporation when the cartridge is removed from the device. The scent-containing article of manufacture, such as cartridge 22, is preferably also reusable and replayable after it has been initially "played" and removed from the device, and is then inserted back into or onto the device.

The scent-containing article of manufacture, such as cartridge 22, can as shown in the drawings, comprise a closed structure which has a single opening therein for the emission of scents. This is believed to provide the cartridge 22 with less likelihood of the possibility of evaporation of the scents contained therein than structures which contain multiple doors or covers, each of which are subject to being opened partially or completely, resulting in evaporation of the scents. It also provides the cartridge 22 with greater protection against tampering. Thus, in the embodiment shown in the drawings, the scents are enclosed when the scent-containing article of manufacture is removed from the device, and the scents are not accessible from outside the article, such as by the opening of doors covering the scents. In other words, there is a fixed cover that covers one or more of the scent receptacles. In the embodiment shown in the drawings, this fixed cover, outer shell 24 covers all the scent receptacles when the cartridge 22 is removed from the device. It is fixed in the sense that it is not moveable. Of course, in other embodiments, the scent-containing article of manufacture could be provided with one or more doors, or covers, if desired for some particular reason.

The scent-containing article of manufacture, such as cartridge 22, preferably also has one or more sealing mechanisms that seal the scent elements from evaporation. The sealing mechanisms can be internal of the outer shell, or external of the outer shell of the scent-containing article of manufacture. In the embodiment shown in the drawings, the scent-containing article of manufacture comprises a sealing mechanism that seals the scents that are not emitting scents when the article is inserted into or placed on the device and scents are being emitted from the scents in one of the receptacles. It also comprises a sealing mechanism that is capable of sealing all the scent receptacles when the article is removed from the device. Both these sealing mechanisms are of the internal type in that they reside inside the cartridge shell. The scent-containing receptacles are preferably closed with a single sealing mechanism. This single sealing mechanism preferably has only one element thereof that is moved in order to seal all of the receptacles. This can be contrasted with articles that have multiple doors for access to each scent, which have numerous elements that must be closed in order to seal all the scents. This makes the scent-containing article of manufacture more simple and less expensive to manufacture, and may also improve reliability. Of course, in other embodiments, the scent-containing article of manufacture could be provided with a sealing has multiple components , or undergoes movement of more than one element in order to perform its sealing function.

The scent-containing article of manufacture, such as cartridge 22, preferably also comprises a locking mechanism which is capable of locking and unlocking the article of manufacture. The locking mechanism preferably prevents access to the scent elements when the cartridge 22 is removed from the device. The locking mechanism preferably cooperates with the sealing mechanism. The sealing mechanism has a first sealed position and a second opened position. In the embodiment shown in the drawings, the scent-containing article of manufacture preferably cannot be removed from the device until the sealing mechanism is in its first sealed position. The scent-containing article of manufacture preferably also comprises a "blank" section which does not have any scents provided thereon or therein. The "blank" section provides a start and stop position for emitting scents from the scent-containing article of manufacture.

The scents in the cartridge 22, may have, and preferably do have, an overall theme or physiological effect. The term "theme", as used herein, generally refers to scents that are related solely to one or more of the other scents contained in or on the article of manufacture, rather to scents that are designed to be emitted simultaneously with other media, such as film, music, theatre, art, etc., and relate to such other media. That is, when a "theme" is referred to herein, the theme can be derived from, or supported by, or based on only the scents in the multiple scent-containing article of manufacture, rather than events taking place simultaneously in some other media. However, if desired, the themes referred to herein can relate generally to other media, such as film, music, theatre, art, etc., without emitting scents simultaneously with events taking place in such other media so long as the scents are related to each other in the manner described herein. Further, certain aspects of the present invention are also believed to be novel when the scents are emitted simultaneously with the events taking place in some other media. Therefore, the present invention does not exclude the use of scents emitted simultaneously with other media where these aspects of the invention are concerned.

Examples of themes include, but are not limited to: floral themes; themes related to a pleasant location such as sylvan, flowery garden, forest, field, sea, or mountain themes; themes for relaxation; themes for stimulation; other aromacological themes providing physiological effects; themes relating to various times of the day (such as for waking up in the morning); scents from various countries, states, cities or geographical regions, such as scents of the Orient; and seasonal themes, such as seasons of the year, or holiday seasons, and the like; spiritual themes, e.g., relating to meditation, inspiration, and serenity, such as incense and sandalwood; themes relating to religion and/or worship, with scents such as frankincense, other incenses, myrrh and floral themes such as rose, dogwood, lily, and the like; aromatherapy themes; themes relating to ethnicity, themes relating to food (e.g., scents of a bakery, scents of a kitchen, scents of a donut shop, scents of a Thanksgiving dinner); themes relating to nature; themes relating to historical events (e.g., the Battle of Gettysburg, Marie Antoinette at Versailles, ancient Rome); themes relating to sporting and other events (e.g., the World Series); themes relating to memories (school days, Grandma's kitchen, a 1950's diner restaurant); themes relating to celebrations (e.g., New Year's Eve); themes relating to literature; themes relating to artists; themes relating to celebrities/famous figures; themes relating to color; romantic themes (e.g., scents similar to those in candles); themes relating to a sound track (e.g., to generally remind the user of a movie, a video, or a song, without being choreographed to emit scents on the occurrence of an event, or particular scene in a movie or video); themes relating to artwork (e.g., famous paintings); and themes relating to, or for encouraging the sale of products (e.g., scents of coffees of the world emitted from a device placed in the coffee section of a store which sells coffee, or scents of fine fragrances and/or cosmetics for encouraging the sale of these products). Any number of scents can share the common theme. In certain embodiments, at least half of the scents in the cartridge share a common theme. In other embodiments, all of the scents in the cartridge share a common theme.

In still other embodiments, a number of the scents contained in the cartridge are related to each other, such that they comprise a general type of scent (e.g., floral, etc.) even though the cartridge may not have an overall theme. Any number of the scents may be related in such a manner. In these embodiments, the scents may, for example, comprise any of scents of the various types described above in conjunction with the discussion of the themes.

The cartridge 22, or any portion thereof, such as the top surface 26 can have one or more illustrations, colors, icons, and/or writing 41 thereon for various purposes. The cartridge 22 may have an illustration which represents the "theme" of the scents in the cartridge, such as a forest, or floral theme. The cartridge 22 may also have a listing of the scents contained therein and the "track" on which they are found. Although the illustration, color, icon, and/or writing 41 is represented in the drawings by a rectangular area shown with dashed lines, it should be understood that the illustration, color, icon, and/or writing may cover all or any portion of the cartridge 22.

Figure 7:
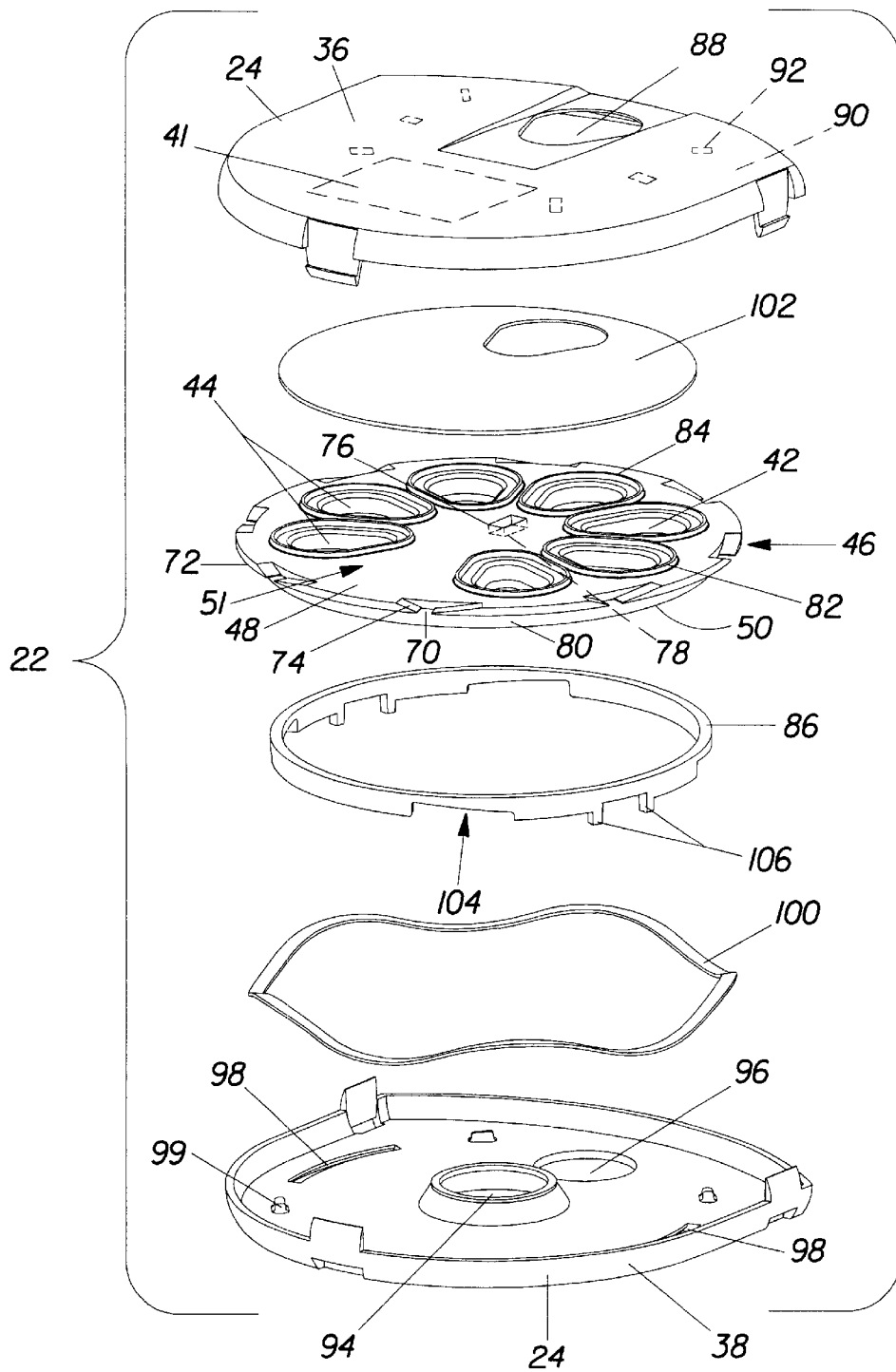
FIG. 7 is an exploded perspective view showing the components of the cartridge shown in FIG. 3.

FIG. 7 shows the construction of this embodiment of the cartridge 22 in greater detail. The cartridge 22 contains multiple scent elements (or scents, aromatic materials, fragrances, or perfumes) 42 that are disposed on a multiple scent-containing component. The multiple scent-containing component can be provided in any suitable configuration, and may have any suitable shape, including, but not limited to any of the shapes described above in conjunction with the description of the scent-containing article of manufacture. In the embodiment shown in the drawings, the multiple scent-containing component is a circular rotatable disk 46, and the scent elements are disposed in receptacles or holders, such as depressions, reservoirs, or pockets 44 formed in the rotatable disk 46.

This disk 46 is contained inside the shell of the cartridge 24 between the upper portion 36 and lower portion 38 thereof. The disk has a top surface 48 and a bottom surface 50. The top surface 48 of the disk has the pockets 44 formed therein. Any suitable number of pockets 44 can be provided, and the pockets 44 can be in any suitable shape. A non-limiting example of a range for the number of pockets 44 (and, thus, the number of scents contained in the cartridge) is between two and twenty, or more. In the embodiment shown in the drawings, there are seven pockets 44, and a blank space 51 between two of the pockets 44 for when the cartridge 22 is not intended to emit scents. Some non-limiting examples of suitable shapes for the pockets 44 include: rectangular, triangular, trapezoidal, tear-drop shaped, or pear shaped. In the embodiment shown in the drawings, the pockets 44 are pear shaped.

The pockets 44 for the scents in the embodiment shown in the drawings, provide one opening, a top opening, for contact with and emission into the air flowing over the top opening. This is in contrast to structures in which the airstream into which the scents are emitted passes through the scent-containing compartments. Of course, other embodiments could be provided in which the airstream into which the scents are emitted passes through the receptacles. Other embodiments can also be provided where the opening for emission of the scents is located somewhere other than on the top of the pockets 44.

The pockets 44 for the scents can be of any suitable size. In one non-limiting embodiment, the pockets 44 have a length (parallel to the longitudinal centerline L) that is less than or equal to about 1.25 inches (about 3 cm) and a width (parallel to the transverse centerline T) that is less than or equal to about 2 cm.

The scent elements can be provided in any suitable form. In some embodiments, the scents are provided by scent elements comprising perfume, such as perfume oils, that are incorporated onto or into a suitable carrier. The carriers can be provided in the following non-limiting forms: a solid, a liquid, a gel, beads, encapsulates, wicks, a carrier material, such as a porous material impregnated with or containing the scent, and combinations thereof. Preferably, the carrier is in the form of a gel which together with the perfume, forms a gel composition. Gels are preferred because they are less likely that liquids to separate into distinct physical phases when heated. Two non-limiting examples of gels that can be used are hydroxypropyl cellulose and fumed silica.

The perfumes are formulated into a gel composition to minimize the partitioning effect that occurs when a perfume is heated. The amounts of perfume and gel in the gel composition can vary depending on the particular perfume and the gel. In certain non-limiting embodiments, the gel composition is about 90% perfume and about 10% hydroxypropyl cellulose or about 93% perfume and about 7% fumed silica, although other ratios are clearly contemplated. There are a variety of hydroxypropyl cellulose/silica ratios that may be used in combination in the gel composition as well as other appropriate gelling agents.

The scent elements can comprise any suitable perfume. The intensity of the perfume can be evaluated, and the perfume can be diluted if it is found to be too strong. If desired, the perfume can be diluted with solvents such as dipropylene glycol, triethyl citrate, or other appropriate solvents at varying levels. One non-limiting example of a range within which the perfumes can be dilusted is that the perfumes can be diluted to between 0 (i.e., original undiluted perfume concentration) and 50%, by weight.

Preferably, the scent-containing articles of manufacture provide a variety of perfumes with intensities that fall into similar intensity ranges. In other words, in one optional but preferable aspect of the invention, the gel compositions are "normalized" so that there is an equivalent intensity of scent experience for each gel in the article of manufacture. In such embodiments, the gels can also be "normalized" so that there is the ability to adjust the scent intensity at approximately equal levels in the different gels throughout use of the scent-containing article. This will ensure that the intensity of one or more of the scents will not be significantly higher than that of other scents when the intensity control is adjusted.

The gels can be normalized as follows. The gels are formulated with perfumes that have been evaluated for intensity to minimize significant variations in the scent experience across gels. The gel compositions are evaluated against the other gel compositions in the same article by expert sensory graders for intensity. For example, the expert sensory graders can evaluate the intensity of the scent or perfume at a distance of two meters from the device. The following grading scale is used:

5=extremely intense
4=very intense
3=moderately intense
2=weakly intense
1=very weak intensity but still perceptible
0=not perceptible If a fragrance falls in the same range of intensity (+/−1 grade difference) as the other fragrances of that particular series it is considered to be normalized.

To further ensure this normalization, the gel compositions can be heated for a set period of time and evaluated against the other gel compositions in the same manner. This procedure will ensure that the user will experience the same level of scent from each of the gel compositions in a given scent-containing article of manufacture.

The scent elements, e.g., in the form of a gel composition, 42 can be placed directly into the pockets 44 of the disk 46, or into some other receptacle, container, or liner, and this other receptacle, container, or liner with the scent element therein, can be placed into the pockets 44.

Figure 8:
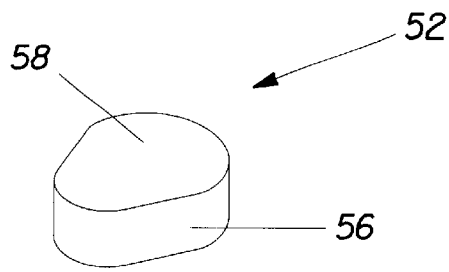
FIG. 8 is a perspective view of one non-limiting embodiment of a receptacle, container, or liner for containing the perfumes.

If the scent element 42 is placed into some other receptacle, container, or liner, such a receptacle, container, or liner can have any suitable configuration, and be comprised of any suitable material. FIG. 8 shows one non-limiting embodiment of a receptacle, container, or liner 52 for containing the scent elements. The receptacles, containers, or liners can be of any suitable size. In one non-limiting embodiment, the receptacles, containers, or liners are pear-shaped and have a length that is less than about 1.25 inches (about 3 cm) and a width that is less than about 2 cm.

Figure 9:
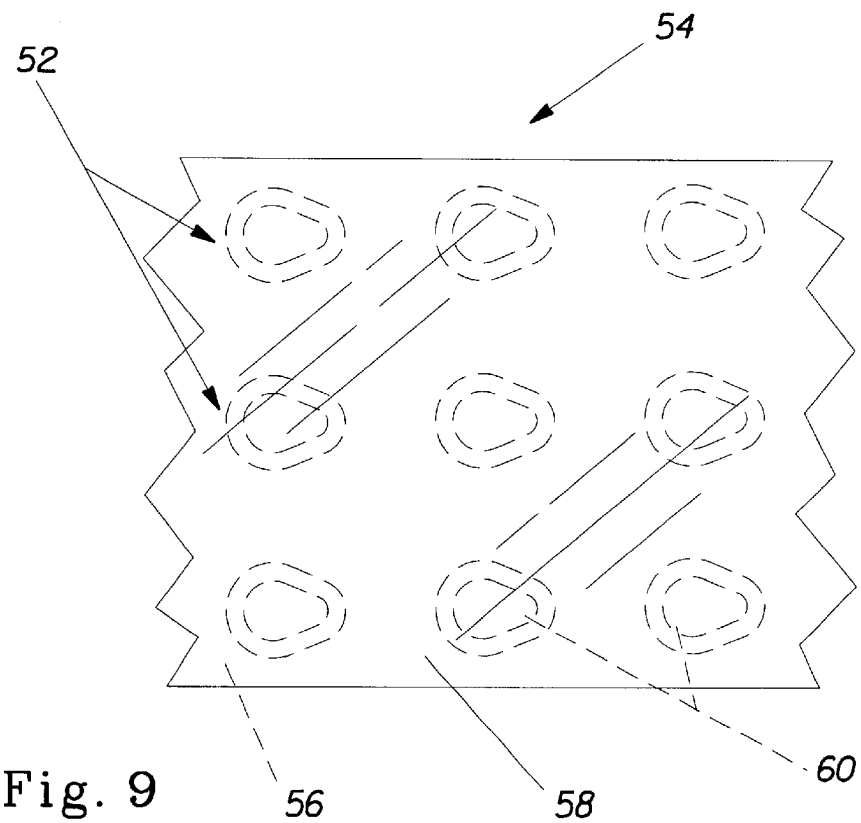
FIG. 9 is a top plan view of one embodiment of an article from which receptacles, containers, or liners for containing the perfumes are made.

FIG. 9 shows one embodiment of an article from which receptacles, containers, or liners 52 for containing the scent elements 42 are made. The article shown in FIG. 9 comprises multiple receptacles 52 for containing the scent elements. The multiple receptacles 52 can be joined together in any suitable manner (partially, or completely) during manufacture. In the embodiment shown in FIG. 9, the multiple receptacles 52 are joined together in the form of a continuous sheet or strip 54. The continuous sheet or strip is later cut into individual receptacles 52.

The continuous sheet 54 comprises a liner portion 56 and a cover portion or membrane 58. The liner portion 56 in this embodiment, comprises a sheet or strip having a plurality of depressions 60 therein which form the bottoms of the receptacles 52 for containing the scent elements 42. While the receptacles 52 can be of any suitable configuration, in this embodiment, the receptacles 52 have the same configuration as the pockets 44 in the disk 46. The receptacles 52 are slightly smaller than the pockets 44 in the disk 46 so that they will be able to fit into the pockets 44.

Figure 10:
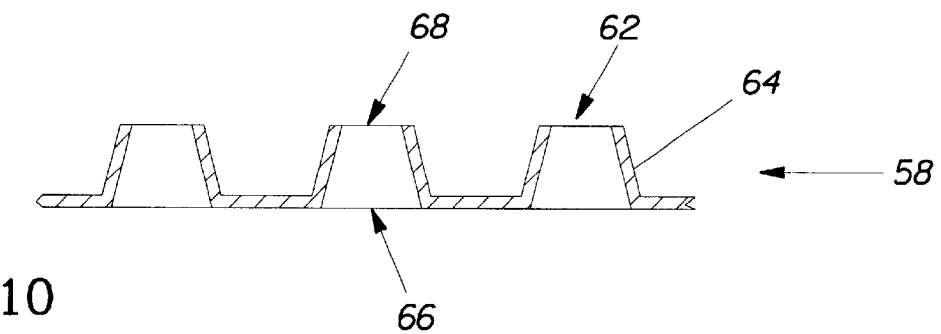
FIG. 10 is a fragmented side view of a three dimensional apertured film suitable for use as the cover portion of the receptacles which may be used to contain the perfumes.

The sheet of receptacles 54 (and, thus, the individual receptacles) can be made from any suitable material, or materials. In one embodiment, the liner portion 56 of the sheet of receptacles 54 is comprised of low density polyethylene (LDPE). The material for the cover portion 58 is preferably selected so that it has minimal impact on perfume emission when the perfume is heated. In one embodiment shown in FIG. 10, the cover portion 58 is comprised of a three-dimensional apertured film that has a plurality of apertures 62 therein that are defined by tapered capillaries 64. The capillaries 64 have a wider portion or base opening 66 and a narrower portion or apex opening 68. The cover portion 58 is preferably oriented so that the narrower portion 68 of the capillaries 64 faces the scent elements so that the vapor from the perfume in the scent elements will readily pass through the cover portion 58, but the perfume gel or liquid will not be inclined to pass through (or leak through) the apertures 62 therein. One example of a material having such tapered capillaries is described in U.S. Pat. No. 3,929,135 issued to Thompson on Dec. 30, 1975. In one embodiment, the cover portion 58 is also comprised of low density polyethylene. Preferably, the cover portion 58 has a porosity of about 540 ft$^3$/min./ft$^2$, and an open area of about 15%, or more.

Placing the scent elements in such receptacles 52 has several advantages. It prevents the perfume gel from contaminating the containment seal, especially if the gel is stored under or subjected to hot conditions which causes phase separation of the gel, and the cartridge 22 or device 20 is inverted, such as during shipping. The receptacles 52 also provide another barrier to prevent the user from contacting the scent elements, such as the gel composition, during use of the device. The cover portion 58 preferably will have minimal effect on the perfume emission. Perfume emission through the cover portion preferably will not cause any partitioning of the perfume thus ensuring scent quality throughout the use of the cartridge 22.

Forming a sheet of receptacles 54 may also simplify and increase the speed of manufacturing in that rather than filling each of the pockets 44 of the rotatable disk 46 with the different scents, a large number of receptacles can be made with the same scent therein in sheet form. This increases the speed with which the individual scent dosages can be made, and reduces the possibility of contaminating the scent pockets 44 with scents which are not supposed to be contained therein. A sheet of receptacles 54 is preferably formed for each scent that will go into the cartridges 22. After the sheets of receptacles 54 are formed, they can be cut to form the individual receptacles 52, and these individual receptacles 52 can simply be dropped into the pockets 44 of the cartridges 22.

The construction of the various components and portions of the cartridge 22 will now be examined in greater detail with reference to FIG. 7. In this regard, however, it should be understood that the cartridge 22 shown in FIG. 7 is but one possible embodiment of the scent-containing article of manufacture. Other types of scent-containing articles can be provided which may not be required to have some or all of the features of the cartridge 22 shown in FIG. 7.

The cartridge 22 shown in FIG. 7 comprises several basic components. These include, from top to bottom: the upper part of the cartridge shell 36; a sealing or barrier material 102 that forms a seal over the pockets 44; the rotatable disk 46; a locking ring 86 for locking and unlocking the cartridge 22; a wave spring 100; and the lower part of the cartridge shell 38. The rotatable disk 46 will be discussed first since, in this embodiment, the other components of the cartridge 22 are designed to cooperate with various features of the disk 46.

In the embodiment shown in FIG. 7, the top surface 48 of the disk 46 preferably has a plurality of slots 70 in the perimeter 72 thereof. The slots 70 are located between the scent pockets 44. On either side of these slots 70, are ramps 74 that gradually increase in depth as the slots 70 are approached. The disk 46 has a small opening 76 slightly offset from the center of the disk 46. This opening 76 that results from the formation of a tooth 78 on the bottom surface 50 of the disk 46. The tooth 78 is used to rotate the disk 46. The small opening 76 is optional, and is merely a result of one process of forming the tooth 78. The bottom surface 50 of the disk 46 preferably comprises a circular rim 80 that is disposed outside of the outer ends 82 of the scent pockets 44. The top surface 48 of the disk 46 comprises gaskets 84 around each of the scent pockets 44 for assisting in the formation of a seal when the scent pockets 44 are not open for use. In the particular embodiment shown, sufficient space is provided between the rim 80 and the outer ends 82 of the scent pockets so permit the locking ring 86 underneath the disk 46 to fit between the rim 80 and the projections which form the outer ends 82 of the scent pockets on the bottom surface 50 of the disk 46. In other embodiments, the locking ring 86 can fit on the outside of the rim 80.

The cartridge 22 has an opening 88 in its top surface 26 (that is, in the upper portion 36 of the cartridge shell) to allow one scent pocket 44 to be rotated into alignment with it and thereby be exposed to allow emission of perfume. The inside surface 90 of the upper portion 36 of the cartridge shell may also have several raised portions (or cams) 92 thereon to reduce wear on the barrier material 102 when the disk 46 rotates. In the particular embodiment shown, there are eight of these raised portions 92 (only six of which are shown for clarity of illustration). The raised portions 92 are disposed radially around the inside surface 90 of the upper portion 36 of the cartridge shell, and are spaced apart so that they will engage with slots 70 in the perimeter 72 of the disk 46 which are located between the scent pockets 44.

The cartridge 22 has four openings in its bottom surface 28 (that is, in the lower portion 38 of the cartridge shell). The openings in the lower portion 38 of the cartridge shell include: an opening in the center 94 to allow the device to turn the rotatable disk 46 inside the cartridge 22; an opening 96 to allow heat from a heating element in the diffuser 20 to transfer to the scent pocket 44 that is exposed for emission; and two slot shaped openings 98 to allow the diffuser 20 to activate and deactivate a locking system inside the cartridge 22 for sealing the scent elements when the cartridge 22 is not in use. The inside surface of the lower portion 38 of the cartridge shell also comprises several projections 99 that interact with ramps 104 on the bottom surface of the locking ring 86.

The cartridge 22 may also contain a resilient element, such as a spring 100 inside the shell 24 that forces the rotatable disk 46 upwards against the barrier material 102 inside the upper portion 36 of the cartridge shell. The contact of the upper surface 48 of the rotatable disk 46 with the barrier material 102 forms a seal that prevents perfume from escaping. The spring 100 can be any suitable type of spring. The spring 100 can be in any suitable location provided it applies a force to create the desired seal. In the embodiment shown, the spring 100 comprises a wave spring that fits outside both the locking ring 86 and the rim 80 on the bottom surface 50 of the disk 46.

The locking ring 86 is located below the rotatable disk 46. The locking ring 86 is a ring with several ramped cutouts 104 therein, and two pairs of ring projections 106. The pairs of ring projections 106 lie on opposing sides of the locking ring 86. The locking ring 86 is rotated by the diffuser 20 to "lock" or "unlock" the cartridge 22 as will be more fully described below. When the locking ring 86 is rotated into the locked position, the rotatable disk 46 is forced against the barrier material 102 with sufficient force to achieve a high quality long-term seal when the cartridge 22 is removed from the diffuser 20. When the locking ring 86 is rotated to the unlocked position, the ramped cutouts 104 on the ring 86 disengage the projections 99 on the inside surface of the lower cartridge shell 38 and allow the rotatable disk 46 to be rotated to expose the scent elements 42 stored in the pockets 44 of the disk 46.

Additional/Alternative Embodiments

Numerous other embodiments of the scent-containing article of manufacture, e.g., cartridge 22, are possible. It should be understood that the following examples of additional and alternative embodiments is not meant to be exhaustive, and that other embodiments are also possible.

In other embodiments, for example, the scent elements need not be heated, and can merely be exposed to the atmosphere, with or without the aid of a fan, to emit the scents.

In these or other embodiments, the seal may be formed with the aid of an element other than a spring. Any suitable resilient element or material may be used in place of the spring. Non-limiting examples of other materials that could be used include a piece of foam and a plastic cantilever structure. In other embodiments, the spring or resilient element can be eliminated altogether, and the locking ring 86 can bias the disk 46 into sealing contact with the seal 102.

In still other embodiments, the article, such as the cartridge can either be a "stand alone" device, or be modified to be, a "stand alone" device that does not require a separate device to emit the scents from the cartridge. For example, instead of using the cartridge in conjunction with a device with all the controls, the cartridge could be modified so that the user could manually select the scent to be emitted. In these or other embodiments, the cartridge could be adapted to plug into a standard electrical wall outlet. Such a plug in cartridge could electrically heat the gels and/or operate in a similar fashion to a plug in appliance timer and periodically change the scent being emitted.

In these or other embodiments, the article of manufacture, such as the cartridge can be altered so that it is re-usable, refillable, disposable or recycleable in many different manners. The article of manufacture can have one or more of these properties (re-usability, refillability, disposability, and be recycleable). The cartridges may be utilized in an environmentally friendly manner. If desired, in any of these embodiments, the design of the article of manufacture (such as the cartridge) may be modified such as by providing a hinge between the upper and lower parts of an outer housing, such as the shell, so that both portions of the housing remain attached, and open like a clam shell, in order to facilitate such uses of the cartridge. Of course, such a clam shell feature is not limited to the cartridge design shown in the drawings, and can be provided on any other articles that are receptive to, or lend themselves to such a feature.

In one set of embodiments, the article of manufacture, such as the cartridge can be reusable or replayable, and then once the scents in the cartridge are completely used, the cartridge can be disposed of, recycled in a municipal waste system, or returned to the manufacturer for recycling.

In another set of embodiments, a portion of the article of manufacture, such as the cartridge can be recycled. This may require the user to open and remove a portion of the cartridge. For example, the cartridge can have a portion, such as a shell or an outer housing, that is opened, and the scent-containing element, such as the rotatable disk, can be removed from the outer housing, and the two portions of the cartridge can be dealt with separately. For instance, the user can recycle the outer housing and dispose of the scent-containing element.

In another variation, the article of manufacture, such as the cartridge can be refillable. In such an embodiment, a portion that goes into the cartridge, such as the rotatable disk, can be provided in a sealed form. For instance, the cartridge can be opened and the rotatable disk removed as described above and a new rotatable disk can be placed into the outer housing. In such a variation, the cartridge and/or the device can be provided with a mechanism for breaking the seal on the scent-containing component, such as the rotatable disk, when it is inserted into the device.

In another set of embodiments, the device into which the scent-containing article is inserted can provide the sealing mechanism, and the scent-containing article can be disposed of after it is used by removing the cartridge from the device.

The scent-containing article of manufactures, such as the cartridges can also be "customized" so that a purchaser of the cartridges can select one or more scents or inclusion in the cartridge.

Thus, in another aspect, the present invention can provide a method of providing ascent-containing article, such as a cartridge to a consumer. The consumer can be an individual consumer and/or a commercial or industrial consumer. The method can comprise: providing a selection of scents to the consumer; obtaining input from the consumer as to the consumer's selection of one or more scents; and providing ascent-containing article, such as a cartridge to the consumer. The method can be carried out in numerous different ways. The method can be carried out at the wholesale level, at the retail level, or at the consumer level.

In these or other embodiments, the scent-containing articles, such as the cartridges can be customized at a store, or at a kiosk, or machine that provides or dispenses scent-containing articles.

In these or other embodiments, the consumer can be provided with a selection of scents through the use of a computer, scratch and sniff samples, or the like. The individual scent receptacles provide the flexibility to supply cartridges in all of these manners without the need to be concerned about contamination of the scent receptacles with scents that are not meant for the scent receptacles.

In any of the embodiments described herein, after the consumer chooses the scents and the sequence of scents, a label listing the scent sequence the customer has chosen can be generated, such as by the printer on a personal computer. The printer can also be programmed to print other information on the label, such as personalized information, which includes, but is not limited to: the name of the buyer, the occasion for the purchase (anniversary, gift, tourist souvenier, etc.) as well as the name of the receiver (if this is a gift) and the occasion. This can be a gift or promotion means for many commercial and/or industrial institutions, such as real estate agents offices, insurance agents offices, banks, supermarkets, department stores, greeting card stores, drug stores, shopping malls, etc. Of course, the features, and methods described herein are not limited to the embodiment shown in the drawings, but instead can apply to any scent emitting devices, as well as any other type of device (even though not necessarily scent emitting) that is capable of being provided with these features, or distributed by these methods.

III. The Device

Figure 11:
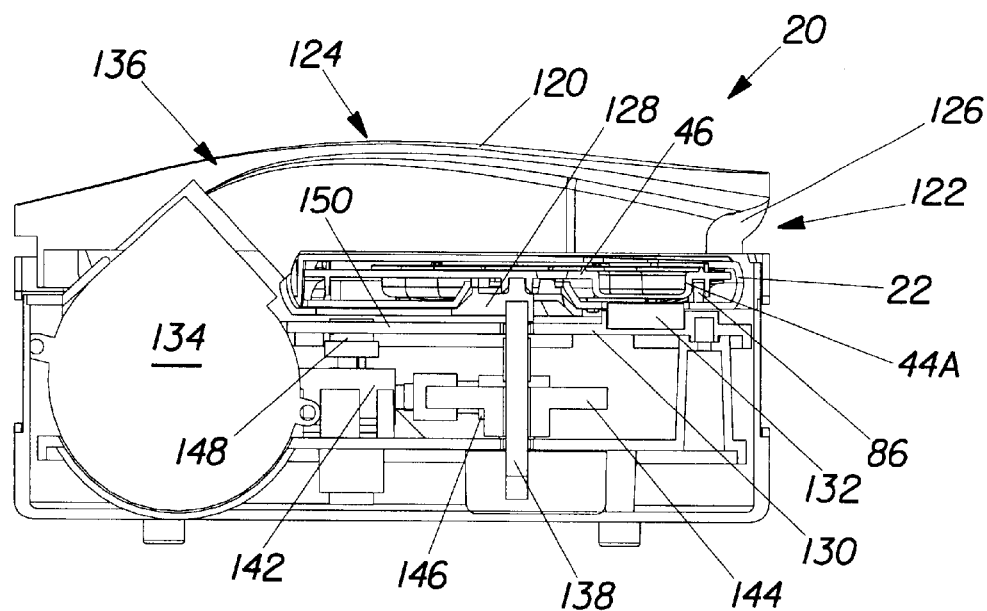
FIG. 11 is a cross-sectional view side view of the scent emitting device shown in FIG. 1 which is taken along line 11—11 in FIG. 1.

The scent emitting device (or apparatus, or simply the "device") or diffuser 20 can be in any suitable configuration. The diffuser 20 is shown in FIGS. 1, 2, and 11. In the embodiment shown in the drawings, the diffuser 20 is generally cylindrical. The top of the diffuser has a raised air duct 120 and air discharge outlet 122 thereon. The top panel 124 of the diffuser 20 can be transparent so that the user of the device can seen the cartridge 22 inside, and any information thereon.

Numerous other embodiments of the diffuser are possible. It should be understood that the present invention is not limited to diffusers having the configuration shown in the drawings, and in other embodiments, the configuration of the diffuser can differ greatly from that shown in the drawings.

The diffuser 20 may contain a component for activating the scents or aromatic materials from their "resting" state to an activated state. Such a component may include, but is not limited to a component that volatilizes or heats the scents or aromatic materials. The dispensing device may also contain a component, such as a fan, for diffusing or transporting the aromatic materials into the environment or atmosphere.

The diffuser 20 may comprise a mechanism for aligning the heater 132 with one or more of the scent-containing receptacles. In one non-limiting embodiment, the mechanism rotates the receptacles within the multi-scent containing article of manufacture so as to align at least one of the receptacles with the heater. In other embodiments, there may be more than one heating elements under the receptacles. In still other embodiments, the receptacles may remain stationary, and the device may comprise a mechanism for rotating or otherwise moving the heating element to align it with the receptacles.

FIG. 11 is a cross-sectional view of the diffuser shown in FIGS. 1 and 2. The embodiment of the diffuser 20 shown in the drawings comprises several primary elements including a slot 126 for receiving the cartridge 22, a rotating hub 128 for engaging and rotating the rotatable disk 46 inside the cartridge 22, a rotating plate 130 to engage the locking ring 86 inside the cartridge 22, an activating component such as a heating element 132 to accelerate diffusion of the perfumes, and a diffusing component such as a fan 134 that cooperates with the ductwork, such as the raised air duct 120 to flow forced air over the exposed pocket 44A of scent gels in the rotatable disk 46. The slot 126 for receiving the cartridge 22 is preferably integrated with a door 136 that can be opened to remove the cartridge 22. This door 136 is preferably controlled by the electronics in the device 20 to ensure that the cartridge 22 can not be removed if it is either unlocked or if ascent pocket 44 is exposed.

The heating element 132 should preferably be in proximity to the scent pocket 44A that is exposed for emission. The heating element 132 need not contact the scent pocket 44A. However, if desired, the heating element 132 may not only be in proximity of the scent pocket 44A, but may also contact the scent pocket 44A that is exposed for emission to increase the transfer of heat from the heating element 132 to the perfume gel in the scent pocket 44.

In this embodiment, the disk 46 inside the cartridge 22 is turned around (rotated) by a shaft 138 having the hub 128 which engages the tooth 78 on the underside of the disk 46. The shaft 138 is connected to a motor 142 through a pair of gears, which comprise a main gear 144 and a worm gear 146. The main gear 144 in this embodiment is a plate gear. The motor 142 rotates the worm gear 146 and the worm gear 146 turns the main gear 144. The main gear 144 rotates the shaft 138 and turns the disk 46 in the cartridge 22 around.

When the cartridge 22 is outside the device 20, the cartridge 22 will be in a locked position with the blank portion 51 of the rotatable disk 46 with no scent receptacle therein in position below the opening 88 in the top portion of the cartridge 22. The spring 100 keeps a lower quality seal in place, but still allows the rotatable disk 46 to rotate. When locking ring 86 is engaged (such as when the cartridge 22 is removed), a higher quality seal is formed which does not permit the rotatable disk to rotate, for greater safety. The pins or prongs 106 in the locking ring 86 pass through the slots 98 in the bottom of the cartridge 22, and engage the locking mechanism on the device 20.

FIG. 11 also shows the components of the diffuser 20 that lock and unlock the cartridge 22. In the embodiment shown, the components that lock and unlock the cartridge comprise a separate motor and set of gears, and a pair of pins, locking pins 140. The second set of gears comprises a gear 148 and a plate gear 150. The motor and gear arrangement rotates the locking pins 140 back and forth to lock and unlock the cartridge. The locking pins 140 are on the plate gear 150, which is also connected to the shaft 138. In the embodiment shown, the locking pins 140 (which are oriented into the plane of the page on the drawing sheet) are disposed so that they will fit inside the curvilinear slots 98 in the bottom of the cartridge 22. The locking pins 140 fit between the projections 106 in the circular locking ring 86. The ramped cutouts 104 in the circular locking ring 86, as noted herein, have a depth which varies from a low end to a high end so that they form ramps that slide along the projections 99 on the inside surface of the lower cartridge shell 38. When the motor turns the gears, the locking pins 140 turn the locking ring 86 by pushing on the projections 106 in the locking ring 86. When the highest portions of the ramped cutouts 104 align with the projections 99, the locking ring 86 will be in its lowest position. This transfers the load from the locking ring 86 to the spring 100 and compresses the spring 100. This removes pressure at the interface or seal between the barrier material 102 and the rims or gaskets 84 surrounding the scent receptacles 44, and permits the rotating disk 46 to be rotated.

The motors are wired to a circuit board which has the control circuitry, which is linked to the control buttons. The device can be provided with an electrical plug for inserting into an electrical outlet of a structure, vehicle (e.g., automobile cigarette lighter), or the like. Alternatively, the device can be powered with batteries.

The diffuser 20 can have controls for the consumer to start and stop the device, to select the scent "volume" or intensity, to select the time interval between scent transitions, and to skip one or more undesired scents in the cartridge. These can include a start and a stop button, which may be separate, but are preferably a single start/stop button 160, an eject button 162, ascent intensity control 164, a scent duration control 166, and a "skip" button 168 for skipping ahead to the next scent in sequence. It should be understood that the controls described in the preceding sentence are merely one embodiment of the possible controls for the diffuser 20. The diffuser 20 need not have all of these controls, and may have other, or different controls.

The diffuser 20 may also have one or more displays so that the user will be able to determine the control settings. Several non-limiting examples of displays include: ascent intensity display 170, ascent "track" number display 172, and a scent duration display 174. The displays may be in any known form. In the embodiment shown in the drawings, the displays are in the form of liquid crystal display (LCD) or light emitting diode (LED) displays, that display a numeric value. For instance, the numeric value of the scent duration display could display the number of minutes that the scent will continue to be emitted.

In some embodiments, the apparatus can have a single control which controls both the activation of the aromatic materials from a resting state to an activated state, and the diffusion of the aromatic materials into the environment. For instance, a single control may control the operation of both the heater 132 and the fan 134. In the embodiment shown in the drawings, this is the scent intensity control 164.

The components of the device 20 can be made out of any suitable material, and can be in any suitable arrangement. Suitable materials include, but are not limited to metals (e.g., aluminum), glass, or plastic. Preferably, the duct work on the device, such as the raised air duct 120, is made of PET because it has minimal tendency to absorb odors and deform when heated. In addition, the discharge outlet, the heater 132, and the scent receptacle 44A for the scent being emitted are preferably located relatively close to the exterior 40 of the device so as to minimize any tendency for scents to contaminate portions of the device which are "down wind" of the discharge outlet 122.

The heater 132 can be any suitable heater that is capable of heating the perfume gels to the desired temperature. The heater 132 preferably comprises a heating element, which is the part of the heater that becomes hot. The heater 132 can be run at any suitable temperature, and for any suitable duration. In other embodiments, the heater 132 can be omitted altogether, in which case the scents will be diffused from their "at rest" or unheated state by the fan 134.

Other novel aspects of the present invention relate to the ways the device may be programmed to emit the scents or aromatic materials. This will be referred to as the "emission program". The emission program comprises one or more emission periods during which the aromatic materials are emitted, and the manner or manners in which the scents are emitted.

In one embodiment, at least one of the aromatic materials is emitted for an emission period of greater than or equal to about 1 minute and less than 120 minutes. In other embodiments, the emission period may be any range of number of minutes that falls within the aforementioned range. Such other ranges include, but are not limited to a range of between about 1 minute and about 90 minutes, inclusive, and a range of between about 1 minute and about 60 minutes, inclusive. In still other, but less preferred embodiments, the aromatic materials may be emitted for an emission period of less than 1 minute, or greater than or equal to 120 minutes. The aromatic materials can be emitted continuously during the emission period, or intermittently. The scent emission program in preferred embodiments is intermittent, and uses a pulsed sequence of scent emissions for each given scent to minimize "habituation", and for other benefits described in greater detail below. The controls can be set up so that the intermittent emission of the scents can take place with or without the user having control thereof.

The scent emission program preferably provides for user input on the scent intensity and duration. In such preferred embodiments, the user will control scent intensity and duration. Default settings for both these parameters can also be available for "one-touch play". As discussed above, in some preferred embodiments, the system uses a pulsed sequence of scent emissions for each given scent. For example, in one non-limiting embodiment, each scent will be emitted for a series of ten minute periods. In such an embodiment, each ten minute period may have a period when the heater and/or fan is being powered and one or more periods when the heater and/or fan is not being powered. The inputted scent duration will be realized via a multiplicity of intermittent emission periods. An additional non-heated period, such as a five minute period, can be provided for the last portion of the period of a given scent's emission cycle to permit the scent to dissipate before a new scent is introduced. Preferably, such a non-emission period is of a shorter duration than the emission period. Preferably, the non-emission period is less than or equal to one-half the duration of the emission period.

Figure 12:
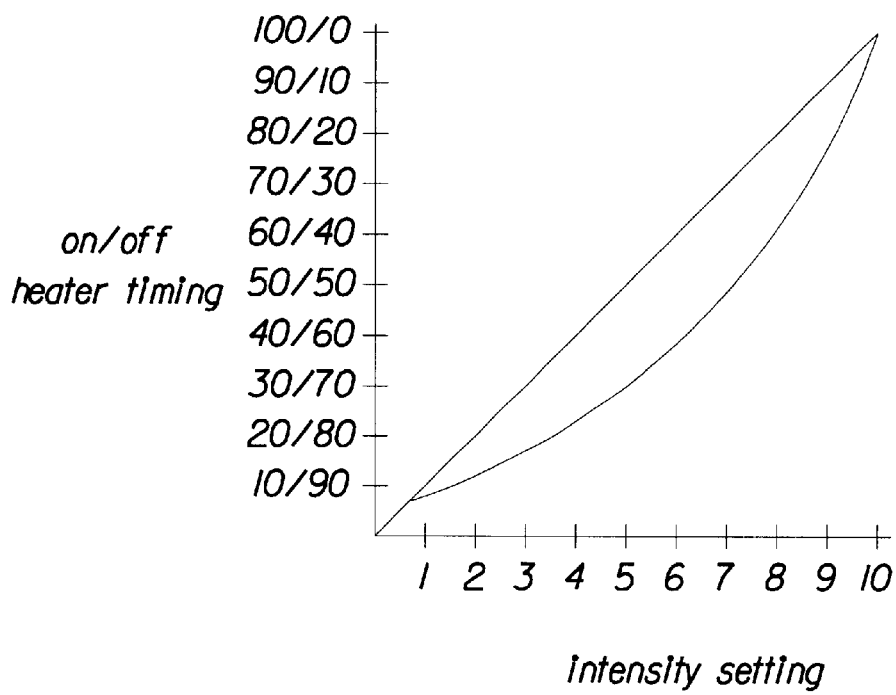
FIG. 12 is a graph that shows one way in which the ratio of the period of time the device heater is on/off may be varied to adjust the intensity of the scent emitted.

The relative proportion of time the heater 132 is being powered to the time it is not being powered during a ten minute emission period will determine the intensity of scent. For example, at a low intensity setting, the ratio of the period of time the heater 132 is on/off may be about 10/90. In contrast, at the highest setting, the ratio may be about 100/0. FIG. 12 is a graph which shows one non-limiting example of the time that the heater is powered during an emission period versus the intensity setting. The upper line in the graph represents a linear relationship between the ratio of the on/off period and the intensity setting. As shown in FIG. 12, the timing and the intensity can be set so that the ratio of the period of time the heater is on/off will increase more at higher settings. This approach provides greater response so the increase in scent intensity will be more noticeable at higher settings and more fine adjustment through the majority of the range.

Figure 13:
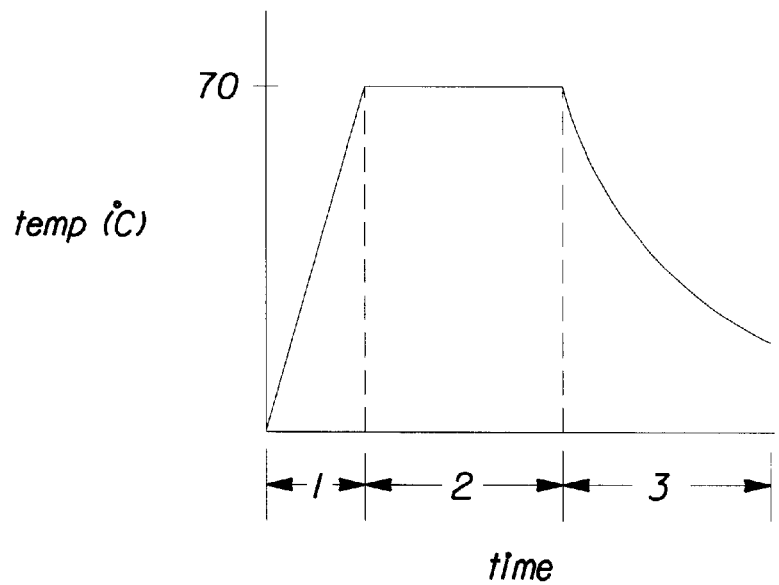
FIG. 13 is a graph that shows one way in which the heater settings and durations at the different settings may be used to quickly bring the heater up to the desired temperature.

The heater 132 can heat the heating element to a temperature within any suitable range for emitting the scents. The heater 132 can, in some embodiments, be set to heat the heating element to a temperature that is lower than normal room temperature (for example, if it is used outside). One non-limiting range of temperatures to which the heater 132 may heat the heating element is between about 20° C. and about 100° C. In one non-limiting embodiment, the heater 132 is powered so that an operating surface temperature of 70° C. is reached quickly and held steady. The heater 132 can be powered so that the operating temperature is reached quickly in a number of different manners. In one embodiment, this is achieved by powering the heater in two distinct steps. FIG. 13 is a graph that shows one way in which the heater settings and durations at the different settings may be used to quickly bring the heater up to the desired temperature. In one non-limiting embodiment, e.g., during the first approximately 30 seconds of a heating period (the period designated "1" in FIG. 13), the heater is powered/pulsed at a relatively high frequency. This allows the heater 132 to warm-up quickly. Subsequently (after the heater reaches the desired temperature, e.g., during the period marked "2"), the frequency is lowered to maintain the target temperature. After a specific period (during the period designated "3"), the heater 132 may be turned off to allow the scent to dissipate.

Figure 14:
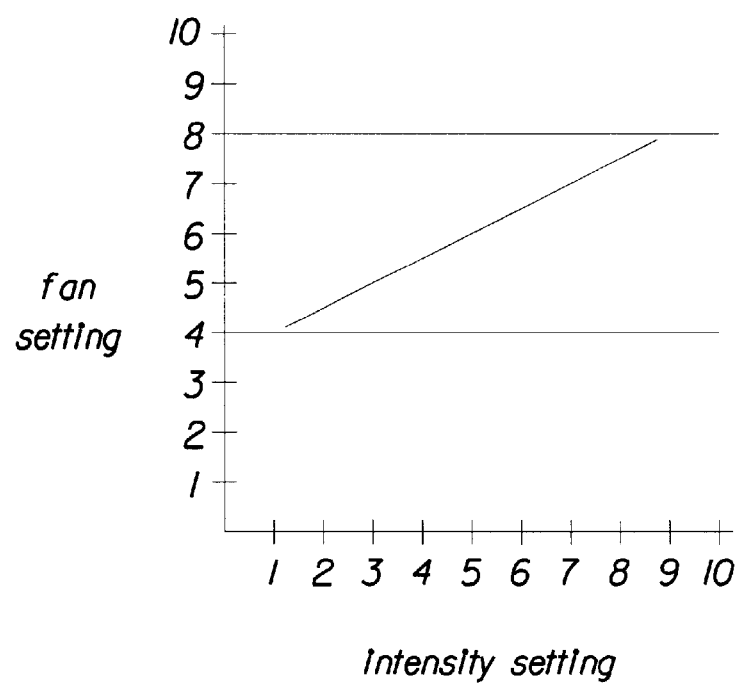
FIG. 14 is a graph that shows one way in which the fan setting can be varied with changes in the intensity setting.

The fan 134 can be set at any desired setting. In one non-limiting embodiment, the airflow generated by the fan 134 will vary as a function of the intensity selected. Because a minimum airflow is required to effect bulk air movement in a typical room, the fan speed scale will, in such an embodiment, preferably begin at an intermediate setting for the fan (e.g., at a fan setting of "4"). FIG. 14 is a graph that shows one way in which the fan setting can be varied with changes in the intensity setting. In this embodiment, the fan speed will climb linearly from the lowest intensity setting to its maximum output (that is, to the lowest fan setting which achieves maximum airflow, which is not necessarily the highest fan setting) at the 80% of maximum intensity setting. This provides good airflow for more than just the highest intensity setting.

The airflow can also be made to vary as a function of the heating program and the resulting temperature. For example, during the period when the heater is being powered and until it cools to about 35° C., the fan speed will be set as described above (see FIG. 14). Below 35° C., the fan speed will be reduced, but the fan will remain on. In one non-limiting example, this setting can be about 20% of the maximum output of the fan. In other words, as long as the system is above 35° C., the fan will be on. The fan also runs to cool the system after the period the heater is being powered, but at a lower speed.

Figure 15:
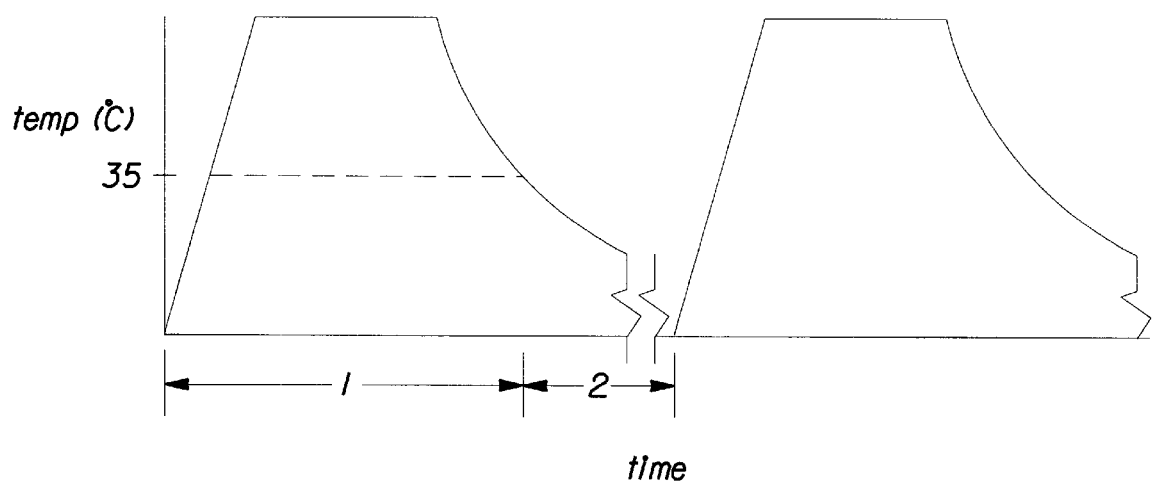
FIG. 15 is a partially fragmented graph that shows one example of an emission cycle.

As mentioned previously, the user will set how long they want each scent to be emitted. FIG. 15 is a graph that shows one non-limiting example of an emission cycle. This period of time shown is divided into a collection of active emitting periods (e.g., the period of time designated "1"), each of which have a final exhausting period (the period of time designated "2"). In the example of the emission cycle shown in FIG. 15, the final exhausting period will last 5 minutes during which the fan will be run at 20% of its maximum output. Two distinct approaches are employed based on the time selected by the user. If the time is less than 15 minutes (leaving less than 10 minutes for the emitting period), a single emitting period is defined by the time selected by the user ("t") minus the five minute exhaustion or dissipation period (t−5) and the proportions defined in the intensity program are applied to t−5. If t−5 is greater than or equal to 10 minutes, then t−5 is divided by 10 to define n, the number of emitting periods for a given scent's duration. If t−5 is not directly divisible by 10, the remaining fraction of time less than 10 is divided evenly into the whole periods, n. The ratios in the intensity program are then applied to the n periods greater 10 minutes. For example, if the inputted scent duration time is 40 minutes, n=3 each lasting 10+5/3 minutes.

The emission program described above provides a number of advantageous features. The user is provided with control so that the scents emitted are tunable to accommodate personal preferences and room environment, for instance to provide "just enough" scent. The emission program can provide a gentle intensity modulation and exhausting sequence with each scent to modulate the intensity of scent to reduce scent "fatigue" or habituation. The quality of the scents is better preserved throughout the use of the cartridge. By emitting scents strategically, and/or by only heating enough so as not to age the perfume, scent quality is maintained longer. The emission program preferably also minimizes residual scent in the air/on surfaces. The emission program preferably provides noticeable transitions between different scents, and allows the scents to dissipate after use. This is in contrast to known plug in devices which can leave ascent is on carpets and other surfaces after use.

Numerous alternative embodiments of the emission program are possible. The scents can be emitted one at a time as described above. Alternatively, more than one scent can be emitted at a time. For examples, the barrier material 102 may have more than one hole therein and/or there can be more than one heater so that the scents can he blended. The scents can be blended in similar proportions, or one scent can be emitted at a lower intensity and provide a "background" scent, and other scents can be "played on top of" the bakground scent.

The device can also be provided with a non-limiting number of other optional features, if desired. It may, for instance, be desirable to provide the device with a light that illuminates a portion of the cartridge, such as the top of the cartridge, so that the user will be able to see any design and/or writing on the top of the cartridge even when it is dark.

The device can be provided with a hand held remote control so that the device can be operated from a distance. The device can also be provided with a timer that will allow the user to program the device to start at a particular time. Preferably, in such an embodiment, the timer is integral with, and built into the device. In other embodiments, a separate timer can be used with the device.

In other embodiments, the device can be used in conjunction with and, if desired, in synchronization with, other media including, but not limited to: sound, light, visual images, water, etc.

In addition, numerous other embodiments of the diffuser are possible. For example, it is also contemplated that other embodiments can be made in which the cartridge is located on the outside of the housing of the diffuser during use.

In other embodiments, the locations of the motors could be reversed and the mechanism for unlocking the cartridge could be located below the mechanism for rotating the disk in the cartridge. In still other embodiments, the same motor could be used to both lock and unlock the cartridge, and rotate the disk 46.

In these or other embodiments, instead of the cartridge having a rotatable disk, the disk could remain stationary and the device can be provided with one or more heating elements (or a plurality of heaters) that lie under, or rotate under the scent-containing receptacles. Of course, in any of the embodiments described herein, the heater could be dispose over, or adjacent to the scent-containing receptacles in other embodiments. Other embodiments are also possible.

The intended mode of operation is for the user to place a cartridge 22 into the diffuser 20 and to close the door and press the start button 160. When the cartridge 22 is outside the device, the cartridge 22 will be in a locked position with the blank portion 51 of the rotatable disk with no scent receptacle therein in position below the opening 88 in the top portion of the cartridge 22. The device 20 will first unlock the rotatable disk 46 inside the cartridge 22 and then will rotate the internal rotatable disk 46 in the cartridge 22 to expose the first pocket 44A containing scent gels. The heating element 132 below the pocket 44A will energize and accelerate the emission of perfume. The fan 134 will then be started, forcing air through a duct 120 and past the exposed pocket 44A containing gels 42. This air will then enter the room and diffuse the scent quickly throughout the environment. After a pre-determined interval, the fan 134 and heating will be stopped and the disk 46 will be rotated to expose the next scent pocket 44. The fan 134 and heater 132 will then restart and emit the next scent. Pauses or breaks in the emission process can be programmed into the device 20 to ensure that it does not emit an excessive amount of perfume into the room.

When the user wants to turn the device 20 off, the start/stop button 160 is pressed and the device 20 first rotates the disk 46 inside the cartridge 22 back to the closed position so none of the pockets 44 are exposed to the outside. The locking ring 86 is then rotated to the locked position to hold the disk 46 shut against the sealing barrier 102 on the inside of the cartridge 22. After this has been completed, the door of the device opens and the user may remove the cartridge. Thereafter, the cartridge 22 may be re-used at a later time if there is still perfume left inside the pockets.

The device 20 may also be provided with instructions for using the same. The instructions may include instructions for setting the device based on the size of the room, vehicle, etc. in which the device is placed. The instructions may also include instructions for setting the device for the desired durations for emission or non-emission of each individual scent. For example, the instructions could provide that the duration of scent emission should be relatively short if the user desires to be more aware of the scents, e.g., to minimize "habituation"; or, that the duration should be relatively long if it is desired for the scents to remain more in the "background". Instructions for recycling the article of manufacture, such as the cartridge, or portions thereof can also be provided. Instructions to insert the cartridge into the clam shell can also be provided. Instructions to arrange the play sequence of perfumes/gels for an optimum scent experience can also be provided. The instructions can be provided in any suitable form, e.g., written, audio, and/or video.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An apparatus for diffusing aromatic materials contained in or on an article of manufacture which article comprises multiple aromatic materials, said apparatus comprising:
   a housing; and
   a removable, reusable/replayable, closed, multiple scent-containing article of manufacture, said multiple scent-containing article of manufacture comprising a plurality of receptacles for retaining multiple aromatic materials, said article having a sealed state so that said aromatic materials remain sealed from evaporation when said article is removed from said housing, wherein the multiple scent-containing article is removably inserted into or onto said housing.

2. The apparatus of claim 1 wherein the multiple scent-containing article comprises a closed structure having a single opening therein for the emission of said scents.

3. The apparatus of claim 1 wherein the receptacles of said multiple scent-containing article are closed with a single sealing mechanism that seals said receptacles when said article of manufacture is not in use.

4. The apparatus of claim 1 wherein the receptacles of said multiple scent-containing article are closed by a single movement of a sealing mechanism that seals said receptacles when said article of manufacture is not in use.

5. The apparatus of claim 1 further comprising a locking mechanism capable of locking and unlocking the scent-containing article of manufacture.

6. The apparatus of claim 1 further comprising a sealing mechanism having a first sealed position and a second opened position, wherein article of manufacture cannot be removed from said housing until said sealing mechanism is in its sealed position.

7. The apparatus of claim 6 wherein said aromatic materials are enclosed when said article is removed from said housing and are not accessible from outside said article.

8. The apparatus of claim 1 wherein said article further comprises a blank section which does not have scents provided thereon or therein, wherein said blank section provides a start and stop position for emitting said aromatic materials from said article of manufacture.

9. The apparatus of claim 2 wherein said article of manufacture comprises multiple scent-containing receptacles wherein said single opening is disposed so that the air into which said aromatic materials will be emitted passes adjacent to, rather than through, said receptacles.

10. An apparatus according to claim 1 wherein said multiple scent-containing article of manufacture comprises a cartridge.

11. An apparatus according to claim 1 wherein said multiple scent-containing article of manufacture comprises a disc.

12. The apparatus of claim 1 wherein the multiple scent-containing article of manufacture has a configuration selected from the group consisting of: disc-shaped, oval, parallelepiped-shaped, rectangular, cube-shaped, cuboid-shaped, cylindrical-shaped, pyramid-shaped, spherical-shaped, or irregularly-shaped.

13. The apparatus of claim 1 having emission settings wherein at least one of the aromatic materials is emitted for an emission period of greater than or equal to about 1 minute and less than 120 minutes.

14. The apparatus of claim 13 wherein at least one of the aromatic materials is emitted for an emission period of between about 1 and about 60 minutes, inclusive.

15. The apparatus of claim 13 wherein at least one of said aromatic materials is emitted continuously during said emission period.

16. The apparatus of claim 13 wherein at least one of said aromatic materials is emitted intermittently during said emission period.

17. The apparatus of claim 13 which is set to shut off for a non-emission period that is of a shorter duration than said emission period.

18. The apparatus of claim 17 wherein said non-emission period is less than or equal to one-half of the duration of the emission period.

19. The apparatus of claim 1 further comprising a heater for heating the aromatic materials.

20. The apparatus of claim 19 further comprising a mechanism for rotating the receptacles within the multiple scent-containing article so as to align said at least one receptacle with the heater.

21. The apparatus of claim 19 wherein the heater for heating the aromatic material is provided with a heating element that is heated to a temperature between about 20° C. and about 100° C.

22. The apparatus of claim 19 wherein the heater heats at least one of the aromatic materials for an emission period of greater than or equal to about 1 minute and less than 120 minutes.

23. The apparatus of claim 19 wherein the heater heats at least one of the aromatic materials for an emission period of between about 1 and about 60 minutes, inclusive.

24. The apparatus of claim 22 wherein said heater is set to run continuously during said emission period.

25. The apparatus of claim 22 wherein said heater is set to run intermittently during said emission period.

26. The apparatus of claim 22 wherein said heater is set to shut off for a cool down period that is of a shorter period than said emission period.

27. The apparatus of claim 26 wherein said cool down period is less than or equal to one-half of the duration of the emission period.

28. The apparatus of claim 22 wherein after heating said at least one of said aromatic materials for said period of time, the apparatus seals the aromatic material being emitted, and prepares to emit another aromatic material.

29. The apparatus of claim 19 wherein said receptacle comprises a staging area in which a portion of the aromatic material in the reservoir is heated while the remainder of the aromatic material is not directly subject to heat.

30. The apparatus of claim 1 which is provided with a control for the user to control the duration of the emission of the aromatic materials.

31. The apparatus of claim 30 wherein the control allows the user to provide the same emission period for the different aromatic materials, or a different emission period for the different aromatic materials.

32. The apparatus of claim 30 further comprising a computer program wherein the apparatus has a control which is controlled by the computer program to allow the user to program the order in which the different aromatic materials are emitted.

33. The apparatus of claim 1 further comprising a timer integrated therein which allows the user to set the time for the apparatus to turn on and/or off.

34. The apparatus of claim 1 further comprising a control that allows user to skip one or more of the aromatic materials.

35. The apparatus of claim 1 having a single control which controls both the activation of the aromatic materials from a resting state and the diffusion of the aromatic materials into the environment.

36. The apparatus of claim 35 further comprising heater for activating the aromatic materials and a fan for diffusing the aromatic materials into the environment wherein said single control controls both the heater and fan.

37. The apparatus of claim 1 further comprising a hand held remote control so that said apparatus can be operated from a distance away from said apparatus.

38. An apparatus for diffusing aromatic materials contained in a cartridge comprising multiple aromatic materials, said apparatus comprising:
   a housing; and
   ascent-containing cartridge comprising:
      a shell; and
      a disk rotatably mounted inside said shell, said disk comprising a plurality of scent receptacles for containing at least one scent element.

39. An apparatus for diffusing aromatic materials contained in or on an article comprising multiple aromatic materials, said apparatus comprising:
   a housing; and
   a removable, interchangeable, closed, multiple scent-containing article, said multiple scent-containing article comprising a plurality of receptacles for retaining multiple aromatic materials, said article having a sealed state so that said aromatic materials remain sealed from evaporation when said article is removed from said housing, wherein the multiple scent-containing article is removeably inserted into the housing; and
   a mechanism for locking and unlocking the article, said mechanism being capable of unlocking all of said receptacles simultaneously.

40. The apparatus of claim 39 wherein the article has a hole therein and said mechanism for unlocking the article comprises at least one projection that passes through the hole in said article.

41. The apparatus of claim 39 wherein when the article is locked, the aromatic materials cannot be accessed through doors or opening elements.

42. An apparatus for diffusing aromatic materials, comprising:
   a housing;
   a removable, interchangeable, closed, multiple scent-containing article, said multiple scent-containing article having a plurality of receptacles therein for retaining aromatic materials, said article having a sealed state so that said aromatic materials remain sealed from evaporation when said article is removed from said housing, wherein the multiple scent-containing article is removeably inserted into or onto the housing;
   an activating mechanism disposed within the housing for at least partially converting at least a portion of the aromatic material within at least one of the plurality of receptacles in the multiple scent-containing article from a deactivated condition to an activated condition, said activating mechanism having an activated state and a deactivated state; and
   a mechanism for aligning said at least one receptacle with the activating mechanism.

43. The apparatus of claim 42 wherein said activating mechanism comprises a heater.

44. The apparatus of claim 42 further comprising a mechanism for locking and unlocking the article.

45. The apparatus of claim 42 wherein the mechanism for aligning said at least one receptacle with the activating mechanism comprises a mechanism for rotating the receptacles.

46. The apparatus of claim 42 wherein the mechanism for aligning said at least one receptacle with the activating mechanism comprises a mechanism for rotating the activating mechanism.

47. An apparatus for diffusing aromatic materials, comprising:
   a housing;
   a removable, interchangeable, closed, multiple scent-containing article, said multiple scent-containing article having a plurality of receptacles therein for retaining aromatic materials, said article having a sealed state so that said aromatic materials remain sealed from evaporation when said article is removed from said housing, wherein the multiple scent-containing article is removeably inserted into the housing;
   an activating mechanism disposed within the housing for at least partially converting at least a portion of the aromatic material within at least one of the plurality of receptacles in the multiple scent-containing article from a deactivated condition to an activated condition, said activating mechanism having an activated state and a deactivated state; and
   a mechanism for aligning said at least one receptacle with the activating mechanism,
   wherein said receptacles are closed by the movement of a single sealing mechanism that seals said receptacles when said article of manufacture is not in use.

48. The apparatus of claim 47 wherein said activating mechanism comprises a heater.

49. The apparatus of claim 47 further comprising a mechanism for locking and unlocking the article.

50. The apparatus of claim 47 wherein the mechanism for aligning said at least one receptacle with the activating mechanism comprises a mechanism for rotating the receptacles.

51. The apparatus of claim 47 wherein the mechanism for aligning said at least one receptacle with the activating mechanism comprises a mechanism for rotating the activating mechanism.

52. An article of manufacture comprising the apparatus of claim 1 in a package in association with a set of instructions that direct the consumer how to operate the apparatus and/or the multiple scent-containing article correctly, to obtain the desirable olfactory, psychological and/or physiological effects.

53. The article of manufacture of claim 52 wherein said set of instructions for use comprise an instruction for setting the apparatus based on the size of the space in which the apparatus is placed.

54. The article of manufacture of claim 52 wherein the set of instructions for use comprises an instruction for setting the time of scent emission.

55. The article of manufacture of claim 52 wherein said set of instructions for use further comprises an instruction for setting the scent intensity.

56. The article of manufacture of claim 52 wherein said set of instructions for use comprises an instruction for setting the apparatus to arrange the play sequence with the desired duration for emission or non-emission of each individual scent.

57. The article of claims 52, 53, 54, 55, or 56 wherein said set of instructions for use further comprises pictures and/or icons.

58. An apparatus for diffusing aromatic materials contained in or on an article comprising multiple aromatic materials that are related to each other by a common scent theme, said apparatus comprising:
   a housing; and
   a multiple scent-containing article, said multiple scent-containing article comprising a plurality of receptacles for retaining multiple aromatic materials that are related to each other by a common scent theme, said article having a sealed state so that said aromatic materials remain sealed from evaporation when said article is removed from said housing, wherein the multiple scent-containing article is removeably inserted into or onto the housing.

59. The apparatus of claim 58 wherein all of the scents in the multiple scent-containing article of manufacture share a common theme.

60. The apparatus of claim 58 which is not designed to be used simultaneously with other media.

61. The apparatus of claim 58 wherein the common theme is selected from the group of themes consisting of:
   (a) floral and bouquet themes;
   (b) pleasant location themes selected from the group consisting of sylvan, flowery garden, forest, field, sea, or mountain themes;
   (c) themes for relaxation;
   (d) themes for stimulation;
   (e) themes relating to various times of the day;
   (f) scents from various countries, states, cities, or geographies;
   (g) seasonal themes;
   (h) themes relating to food;
   (i) themes relating to nature;
   (j) themes relating to historical events;
   (k) themes relating to other events;
   (l) themes relating to memories;
   (m) themes relating to celebrations;
   (n) romantic themes;
   (o) themes relating to a sound track;
   (p) themes relating to artwork;
   (q) spiritual theme relating to meditation, inspiration, and serenity;
   (r) theme relating to religion and/or worship;
   (s) theme relating to ethnicity;
   (t) themes relating to color;
   (u) aromatherapy themes; and
   (v) themes relating to, or for encouraging the sale of products.

62. The apparatus of claim 59 further comprising at least one illustration, color, icon, and/or writing on the article that indicates the theme of the scents in the article and/or a sequential listing of the scents.

63. The apparatus of claim 59 further being provided with packaging for said article, wherein said packaging comprises an illustration, color, icon, or writing that indicates the theme of the scents in the article and/or a provides a sequential listing of the scents in the article.

64. The apparatus of claim 58 wherein the multiple scent-containing article is removable from said housing and the aromatic materials therein are sealed when said article is removed from said housing.

65. An apparatus of claim 58 wherein the multiple scent-containing article of manufacture comprises a cartridge.

66. The apparatus of claim 58 wherein the multiple scent-containing article of manufacture has a configuration selected from the group consisting of: disc-shaped, oval, parallelepiped-shaped, rectangular, cube-shaped, cuboid-shaped, cylindrical-shaped, pyramid-shaped, spherical-shaped, or irregularly-shaped.

67. An apparatus according to claim 58 wherein the scent-containing article of manufacture comprises a disc.

68. The apparatus of claim 58 wherein the aromatic materials are provided in a form selected from the group consisting of: solids, liquids, gels, beads, encapsulates, wicks, a carrier material impregnated with ascent, and combinations thereof.

69. The apparatus of claim 58 in association with a set of instructions that direct the consumer how to operate the apparatus correctly, to obtain the desirable olfactory, or psychological and/or physiological effects.

* * * * *